US012129255B2

(12) United States Patent
Gillis et al.

(10) Patent No.: US 12,129,255 B2
(45) Date of Patent: Oct. 29, 2024

(54) PYRIDO [2,3-D]PYRIMIDINE DERIVATIVES AS INHIBITORS OF HUMAN IMMUNODEFICIENCY VIRUS REPLICATION

(71) Applicant: VIIV HEALTHCARE UK (No. 5) LIMITED, Middlesex (GB)

(72) Inventors: Eric P. Gillis, Branford, CT (US); Christiana Iwuagwu, Wallingford, CT (US)

(73) Assignee: ViiV Healthcare UK (No. 5) Limited, Stevenage (GB)

( * ) Notice: Subject to any disclaimer, the term of this patent is extended or adjusted under 35 U.S.C. 154(b) by 750 days.

(21) Appl. No.: 17/268,107

(22) PCT Filed: Jun. 17, 2020

(86) PCT No.: PCT/IB2020/055653
§ 371 (c)(1),
(2) Date: Feb. 12, 2021

(87) PCT Pub. No.: WO2020/254985
PCT Pub. Date: Dec. 24, 2020

(65) Prior Publication Data
US 2021/0323967 A1      Oct. 21, 2021

Related U.S. Application Data

(60) Provisional application No. 62/863,406, filed on Jun. 19, 2019.

(51) Int. Cl.
*C07D 487/04*      (2006.01)
*A61K 9/00*      (2006.01)
*A61K 45/06*      (2006.01)
*A61P 31/18*      (2006.01)

(52) U.S. Cl.
CPC .......... *C07D 487/04* (2013.01); *A61K 9/0019* (2013.01); *A61K 9/0053* (2013.01); *A61K 45/06* (2013.01); *A61P 31/18* (2018.01)

(58) Field of Classification Search
CPC ..... A61P 31/18; C07D 471/04; C07D 487/04; A61K 9/0019; A61K 9/0053
USPC ...................................................... 514/258.1
See application file for complete search history.

(56) References Cited

U.S. PATENT DOCUMENTS

2003/0069266 A1    4/2003   Wang et al.

FOREIGN PATENT DOCUMENTS

| RU | 2325389 C2 | 5/2008 | |
| WO | WO-2004014380 A1 | 2/2004 | |
| WO | WO-2018035359 A1 * | 2/2018 | ........... A61K 31/416 |
| WO | 2018/203235 A1 | 11/2018 | |
| WO | 2020/157692 A1 | 8/2020 | |
| WO | 2020/254985 A1 | 12/2020 | |

OTHER PUBLICATIONS

Gillis, et al., Applications of fluorine in medicinal chemistry, *J. Med. Chem.*, 58(21):8315-8359 (2015).
Laplante, et al., Assessing Atropisomer Axial Chirality in Drug Discovery and Development, *J. Med. Chem.*, 54(20):7005-7022 (2011).
Written Opinion, IPOS ( Intellectual Property of Singapore), App. No. 11202113548Q, Third Party Observations, Dec. 19, 2022.
Bastin, et al., "Salt Selection and Optimisation Procedures for Pharmaceutical New Chemical Entities", Organic Process Research & Development 2000, 4, pp. 427-435.
Belikov V.G. Pharmaceutical Chemistry, textbook, 2007, Moscow: "MEDpress—Inform", pp. 27-29.
Belikov, Belikov V.G. Pharmaceutical Chemistry. Textbook. Ed. 4th edition. Moscow: Medpress—inform, 2007, 622 p. (p. 11).
Gavrilov A.S. Pharmaceutical Technology. Preparation of medicinal preparations. Textbook. Moscow: GEOTAR—Media Publishing Group. 2010, 624 p. (p. 20).
Glunz, P. W., "Recent encounters with atropisomerism in drug discovery", Bioorganic & Medicinal Chemistry Letters; vol. 28; pp. 53-60; Oct. 2017.
Kharkevich, D.A. Pharmacology, 10th ed. M.: GEOTAR—Media, 2010, p. 73-74.

(Continued)

*Primary Examiner* — Yih-Horng Shiao
*Assistant Examiner* — Jaret J Crews
(74) *Attorney, Agent, or Firm* — Nora L. Stein

(57) ABSTRACT

The compound and pharmaceutically acceptable salts thereof, and compositions and methods for treating human immunodeficiency virus (HIV) infection are set forth.

21 Claims, 1 Drawing Sheet

(56) References Cited

OTHER PUBLICATIONS

Kummerer, et al., "Pharmaceuticals in the Environment", Department of Environmental Health Sciences, University Medical Center Freiburg, 79106 Freiburg, Germany; Annu. Rev. Environ. Resour. 2010. 35:57-75.
Mashkovsky, et al., Harkevich D.A. Pharmacology, Textbook, 2010, 10th edition, pp. 72-82, M.D. Mashkovsky, Drugs, 14th edition, vol. 1. Moscow, 2001, p. 11.
Mironov, Guideline for Preclinical Studies of Medicinal Products. Part One. Moscow, Griff & K., 2012, 944 p., ed. by A.N. Mironov, pp. 525-548.
Swallow, S., et al., "Fluorine in medicinal chemistry. Progress in Medicinal Chemistry", Elsevier, Edited by G. Lawton, D.R. Witty; 2015, pp. 97-165 (p. 98-103, 115-120, 124-126, 129-130, 140-141, 157-158).
Ting-Chao, "Drug Combination Studies and Their Synergy Quantification Using the Chou-Talalay Method", Cancer Res; 70(2); Jan. 15, 2010, pp. 440-446.
Zhulenko, Gorshkov G.I. Pharmacology. Moscow, KolosS, 2008, pp. 34-35.
PU66776 WO Third Party Observation PCT/IB2020/055653, Oct. 19, 2021.

\* cited by examiner

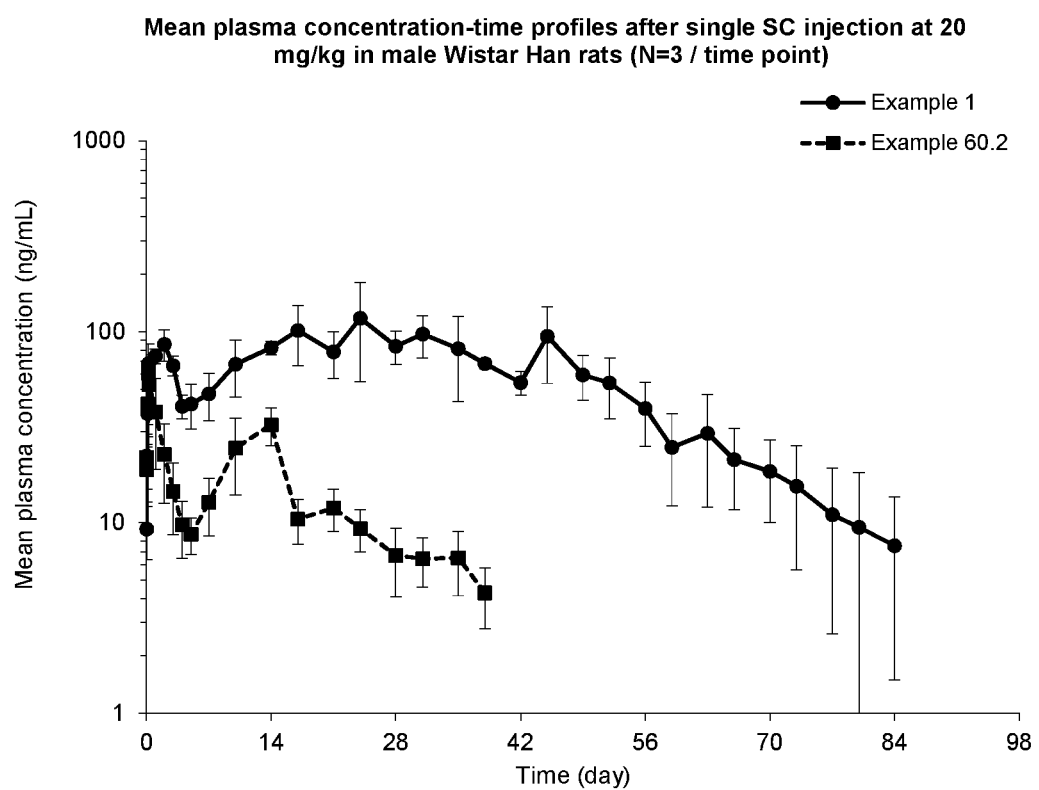

PYRIDO [2,3-D]PYRIMIDINE DERIVATIVES AS INHIBITORS OF HUMAN IMMUNODEFICIENCY VIRUS REPLICATION

This application is a § 371 of International Application No. PCT/IB2020/055653, filed 17 Jun. 2020, which claims the benefit of U.S. Provisional Application No. 62/863,406, filed 19 Jun. 2019.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. In 2015, an estimated 36.7 million people were living with HIV (including 1.8 million children)—a global HIV prevalence of 0.8%. The vast majority of this number live in low- and middle-income countries. In the same year, 1.1 million people died of AIDS-related illnesses.

Current therapy for HIV-infected individuals consists of a combination of approved anti-retroviral agents. Close to four dozen drugs are currently approved for HIV infection, either as single agents, fixed dose combinations or single tablet regimens; the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INSTIs), or entry inhibitors (one, maraviroc, targets the host CCR5 protein, while the other, enfuvirtide, is a peptide that targets the gp41 region of the viral gp160 protein). In addition, a pharmacokinetic enhancer (cobicistat or ritonavir) can be used in combinations with antiretroviral agents (ARVs) that require boosting.

Despite the armamentarium of agents and drug combinations, there remains a medical need for new anti-retroviral agents. High viral heterogeneity, drug-associated toxicity, tolerability problems, and poor adherence can all lead to treatment failure and may result in the selection of viruses with mutations that confer resistance to one or more antiretroviral agents or even multiple drugs from an entire class (Beyrer, C., Pozniak A. HIV drug resistance—an emerging threat to epidemic control. N. Engl. J. Med. 2017, 377, 1605-1607; Gupta, R. K., Gregson J., et al. HIV-1 drug resistance before initiation or re-initiation of first-line antiretroviral therapy in low-income and middle-income countries: a systematic review and meta-regression analysis. Lancet Infect. Dis. 2017, 18, 346-355; Zazzi, M., Hu, H., Prosperi, M. The global burden of HIV-1 drug resistance in the past 20 years. PeerJ. 2018, DOI 10.7717/peerj.4848). As a result, new drugs are needed that are easier to take, have high genetic barriers to the development of resistance, and have improved safety over current agents. In this panoply of choices, novel mechanisms of action (MOAs) that can be used as part of the preferred antiretroviral therapy (ART) can still have a major role to play since they should be effective against viruses resistant to current agents. The improvements that would make drugs easier to take for long periods of time or even for a lifetime could include all or some of the following: reduced side effects, reduced drug-drug interactions, increased duration between dosing, or alternate routes of administration which match to individual patient preferences. The goals of improved safety would definitely include high therapeutic indices towards any toxicities that would cause discontinuation of dosing, and could also include reduced side-effects or reduced drug-drug interactions. The potential to use fewer overall drugs in a combination regimen would also likely lead to improved compliance and safety. Increased potency against the antiviral target, especially if maintained in the presence of human plasma and serum albumin, would also lead to a reduced dose and could directly and positively affect the duration of dosing and the therapeutic index over side effects and toxicities. To summarize, maximum benefits to HIV infected patients would be achieved if anti-HIV drugs with new mechanisms of action were discovered which also have the other benefits described above which facilitate long term compliance and safety.

Certain potentially therapeutic compounds have now been described in the art and set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and PCT Patent applications with the following numbers: WO 2012065062, WO 2013006738, WO 2013006792, WO 2014110296, WO 2014110297, WO 2014110298, WO 2014134566, WO 2015130964, WO2015130966, WO 2016033243, WO2018035359, and WO2018203235.

What is now needed in the art are additional compounds which are novel and useful in the treatment of HIV. Additionally, these compounds should provide advantages for pharmaceutical uses, for example, with regard to one or more of their mechanisms of action, binding, inhibition efficacy, target selectivity, solubility, safety profiles, bioavailability and/or reduced frequency of dosing. Also needed are new formulations and methods of treatment which utilize these compounds.

SUMMARY OF THE INVENTION

Briefly, in one aspect, the present invention discloses the compounds depicted below

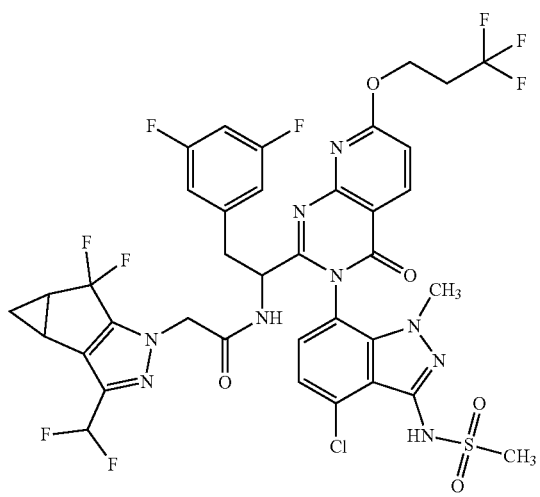 [SMILES: Cn1nc(NS(C)(=O)=O)c2c(Cl)ccc(-n3c(C(Cc4cc(F)cc(F)c4)NC(=O)Cn4nc(C(F)F)c5c4C(F)(F)C4CC54)nc4nc(OCCC(F)(F)F)ccc4c3=O)c21]

and pharmaceutically acceptable salts thereof (hereinafter "compounds and salts of the invention").

In another aspect, the present invention discloses a pharmaceutical composition comprising a compound or salt of the invention.

In another aspect, the present invention discloses a method of treating HIV infection in a human comprising administering a compound or salt of the invention.

In another aspect, the present invention discloses a compound or salt of the invention for use in therapy.

In another aspect, the present invention discloses a compound or salt of the invention for use in treating HIV infection in a human.

In another aspect, the present invention discloses the use of a compound or salt of the invention in the manufacture of a medicament for the treatment of HIV infection in a human.

BRIEF DESCRIPTION OF THE FIGURES

FIG. 1 is a summary of the mean plasma concentration-time profiles in rats in the study described below.

DETAILED DESCRIPTION OF THE INVENTION

Preferably, the compounds and salts of the invention have the stereochemistry depicted below

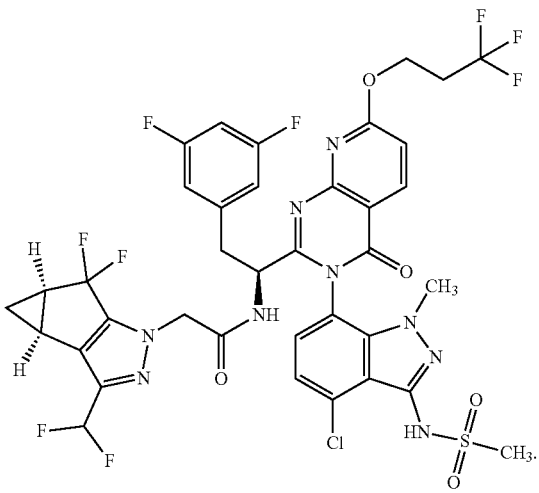 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4nc(OCCC(F)(F)F)ccc4c3=O)c21]

In another aspect, the compounds and salts of the invention have the stereochemistry depicted below

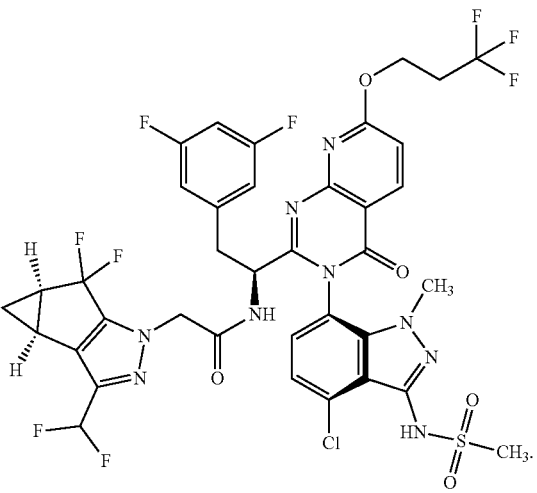

The salts of the invention are pharmaceutically acceptable. Such salts may be acid addition salts or base addition salts. For a review of suitable pharmaceutically acceptable salts see, for example, Berge et al, J. Pharm, Sci., 66, 1-19, 1977.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of the compounds and salts of the invention, and are included within the scope of the invention.

All possible stoichiometric and non-stoichiometric forms of the salts of the compound of the invention are included within the scope of the invention. Acid and base addition salts may be prepared by the skilled chemist, by treatment of a compound of the invention with the appropriate acid or base in a suitable solvent, followed by crystallization and filtration.

The pharmaceutical compositions of the invention further comprise a pharmaceutically acceptable carrier, excipient, and/or diluent. In one embodiment, the pharmaceutical compositions of this invention further comprise a pharmaceutically acceptable excipient.

In the method of this invention, preferred routes of administration are oral and by injection to deliver subcutaneously or intramuscularly. Therefore, preferred pharmaceutical compositions include compositions suitable for oral administration (for example tablets) and compositions suitable for injection, for example subcutaneous or intramuscular injection.

In another aspect the present invention discloses methods of preventing HIV infection in a human or reducing the risk of infection, comprising administering a compound or salt of the invention. Pre-exposure prophylaxis (or PrEP) is when people at risk for HIV infection take daily medicine to lower their chances of getting HIV infection. PrEP has been shown to be effective in reducing the risk of infection. As used herein, "HIV" or "Human Immunodeficiency Virus" refers to HIV-1 and/or to HIV-2.

The compounds and salts of the invention are believed to have as their biological target the HIV capsid and thus their mechanism of action is to modify in one or more ways the function of the HIV capsid. For example, the compounds and salts of the invention may act as capsid inhibitors.

The compounds and salts of the invention may be employed alone or in combination with other therapeutic agents. Combination therapies according to the present invention thus comprise the administration of at least one compound or salt of the invention, and the administration of at least one other agent which may be useful in the treatment of HIV infection. The compounds and salts of the invention and any other pharmaceutically active agent(s) may be administered together or separately and, when administered separately, administration may occur simultaneously or sequentially, in any order. For example, a compound or salt of the invention, and the other agent may be formulated and administered together in a single pharmaceutical composition or may be formulated and administered separately. The amounts of the compound and salts of the present invention and the other pharmaceutically active agent(s) and the relative timings of administration will be selected in order to achieve the desired combined therapeutic effect. The administration in combination of the compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of the compound of the invention, or salts thereof and the other pharmaceutically active agent(s) and the relative timings of administration will be selected in order to achieve the desired combined therapeutic effect.

As such, the compounds and salts of the present invention may be used in combination with one or more agents useful in the prevention or treatment of HIV. Such agents include, for example, nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. Suitable other agents include, for example, abacavir, atazanavir, bictegravir, cabotegravir, darunavir, delavirdine, didanosine, dideoxyinosine, dolutegravir, doravirine, efavirenz, elvitegravir, emtricitabine, etavirine, fosamprenavir, fostemsavir, GSK3640254, indinavir, slatravir, lamivudine, lopinavir, maraviroc, nelfinavir, nevirapine, raltegravir, rilpivirine, ritonavir, saquinavir, slatravir, stavudine, tipranavir, tenofovir, tenofovir alafenamide, tenofovir disoproxil fumarate, zalcitabine, zidovudine, the antibody N6LS, GSK3739937/VH3739937, and S-648414. Additional suitable other agents include Dolutegravir, lamivudine, Fostemsavir, Cabotegravir, maraviroc, rilpiverine, Reyataz, Tenofovir, Afenamide, EfDA, Doravirine, and Preziata. Further suitable other agents include Dolutegravir, lamivudine, Fostemsavir, and Cabotegravir. Preferred agents include, for example, bictegravir, cabotegravir, dolutegravir, fostemsavir, islatravir, and lamivudine. Particularly preferred agents include, for example, bictegravir, cabotegravir, dolutegravir, fostemsavir, and lamivudine.

EXAMPLES

Preparation of bicyclo[3.1.0]hexan-3-ol

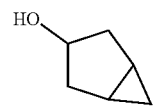

To a stirred solution of cyclopent-3-enol (130 g, 1545 mmol) in DCM (1200 mL) under N2 atmosphere at 0-5° C. was added dropwise a solution of diethyl zinc in hexane (1.0 M, 3091 mL, 3091 mmol) over a period of 3 h. To the solution at 0° C. was added dropwise a solution of diiodomethane (249 mL, 3091 mmol) in DCM (300 mL) over a period of 1 h. The reaction mixture was allowed to warm to 27° C. upon which formation of a white precipitation was observed. The mixture stirred for 16 h. Progress of the reaction was monitored by TLC (SiO$_2$, 20% EtOAc/pet, Rf=0.3, UV-inactive, PMA-active). The reaction mixture was quenched via the careful addition of aq. saturated NH₄Cl solution (1.5 L). The mixture was filtered through pad of Celite. The aqueous layer was extracted with DCM (2×1 L). The combined organic layers were dried over anhydrous Na₂SO₄, filtered and then concentrated under reduced pressure to afford crude bicyclo[3.1.0]hexan-3-ol as red liquid, 180 g. ¹H NMR (400 MHz, CDCl₃) δ=4.41-4.35 (m, 1H), 2.18-2.05 (m, 2H), 1.73 (d, J=13.9 Hz, 2H), 1.35-1.25 (m, 2H), 1.21-1.14 (m, 1H), 0.57-0.43 (m, 2H). GCMS: m/z=98.1).

Preparation of bicyclo[3.1.0]hexan-3-one

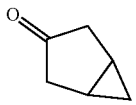

To a stirred solution of bicyclo[3.1.0]hexan-3-ol (210 g, 2054 mmol) in DCM (5000 mL) under N2 atmosphere at 0° C. was added portion-wise Dess-Martin periodinane (954 g, 225 mmol). The mixture was allowed to warm to 27° C. and was then stirred for 16 h. Progress of the reaction was monitored by TLC (SiO₂, 20% Acetone/Hex, Rf=0.3, UV in-active, PMA-active). The reaction mixture was filtered through pad of Celite and the filtrate was washed with aq. NaOH (1N, 8×1 L). The combined aqueous phases were extracted with DCM (5×1 L). The combined organic layers were dried over anhydrous Na₂SO₄, filtered, and then concentrated under reduced pressure (bath temperature: 20° C.) to afford crude bicyclo[3.1.0]hexan-3-one as brown liquid. The liquid was further purified by downward distillation at 70° C. to afford bicyclo[3.1.0]hexan-3-one as a pale-yellow viscous liquid, 125 g (62%). ¹H NMR (400 MHz, CDCl₃) δ=2.61-2.54 (m, 2H), 2.17-2.12 (m, 2H), 1.54-1.46 (m, 2H), 0.92-0.86 (m, 1H), −0.01-−0.08 (m, 1H); GCMS: M/Z=96.1.

Preparation of 2-(2,2-difluoroacetyl)bicyclo[3.1.0]hexan-3-one

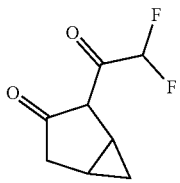 [SMILES: O=C1CC2CC2C1C(=O)C(F)F]

To a stirred solution of bicyclo[3.1.0]hexan-3-one (125 g, 1274 mmol) in THF (1500 mL) under N2 atmosphere at −78° C. was added LDA (2.0 M in THF, 0.701 L, 1402 mmol). The solution was stirred for 1 h at −78° C. To the solution was added slowly over 30 minutes a solution of ethyldifluoroacetate (174 g, 1402 mmol) in THF (300 mL) maintaining a temperature of −78° C. The reaction mixture was allowed to warm to 27° C. and was then stirred for 1 h. Progress of the reaction was monitored by TLC (SiO₂, 20% Acetone/Hexane, Rf=0.3, UV-active). The reaction mixture was quenched via the addition of aq. HCl (1N, 2000 mL). The mixture was stirred for 30 min. and then was extracted with EtOAc (3×1000 mL). The combined organic layers were washed with brine (1000 mL), dried over anhydrous Na₂SO₄ and filtered. The filtrate was concentrated under reduced pressure to afford 2-(2,2-difluoroacetyl)bicyclo[3.1.0]hexan-3-one as a pale-yellow viscous liquid, 180 g (71%). ¹H NMR (400 MHz, CDCl₃) δ=6.18 (t, J=54.8 Hz, 1H), 2.70-2.62 (m, 1H), 2.35 (d, J=19.4 Hz, 1H), 2.14 (br s, 1H), 1.26-1.21 (m, 1H), 1.04-1.03 (m, 1H), 0.22-0.21 (m, 1H), LCMS: M/Z=173.17).

Preparation of ethyl 2-(3-(difluoromethyl)-3b,4,4a,5-tetrahydro-1H-cyclopropa[3,4]cyclopenta[1,2-c]pyrazol-1-yl)acetate

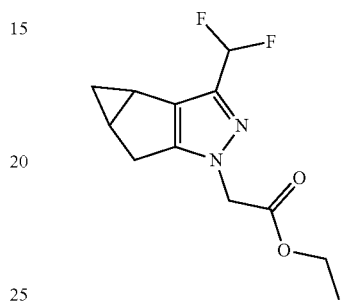

To a stirred solution of 2-(2,2-difluoroacetyl)bicyclo[3.1.0]hexan-3-one (180 g, 910 mmol) in ethanol (2 L) under N2 atmosphere at 27° C. was added ethyl 2-hydrazinylacetate hydrochloride (422 g, 2729 mmol) followed by sulfuric acid (20 mL, 375 mmol). The mixture was stirred for 30 min. and then was heated to 100° C. and stirred for 16 h. Progress of the reaction was monitored by TLC (SiO₂, 20% Acetone/Hexane, Rf=0.3, UV-active). The reaction mixture was concentrated under reduced pressure. The residue was dissolved in EtOAc (2000 mL) and was washed with water (2×1 L), brine (1.0 L), dried over anhydrous Na₂SO₄, filtered, and then was concentrated under reduced pressure. The resulting residue was subjected to silica gel column chromatography (pet.:acetone 100:0→98:2) to afford ethyl 2-(3-(difluoromethyl)-3b,4,4a,5-tetra hydro-1H-cyclopropa[3,4]cyclopenta[1,2-c]pyrazol-1-yl)acetate as an off-white solid, 110 g (46%). ¹H NMR (400 MHz, DMSO-d₆) δ=6.86 (t, J=54.8 Hz, 1H), 4.93 (s, 2H), 4.14 (q, J=7.2 Hz, 2H), 2.88-2.79 (m, 1H), 2.76-2.68 (m, 1H), 2.14-2.04 (m, 2H), 1.19 (t, J=7.2 Hz, 3H), 1.10-1.03 (m, 1H), 0.14 (q, J=4.3 Hz, 1H).

Preparation of ethyl 2-(3-(difluoromethyl)-5-oxo-3b,4,4a,5-tetrahydro-1H-cyclopropa[3,4]cyclopenta[1,2-c]pyrazol-1-yl)acetate

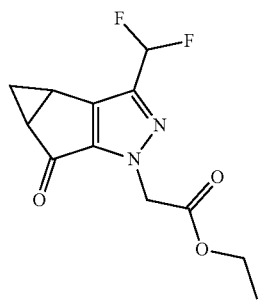 [SMILES: CCOC(=O)Cn1nc(C(F)F)c2c1C(=O)C1CC21]

To a stirred solution of ethyl 2-(3-(difluoromethyl)-3b,4,4a,5-tetrahydro-1H-cyclopropa[3,4]cyclopenta[1,2-c]pyrazol-1-yl)acetate (110 g, 422 mmol) and Celite (395 g) in cyclohexane (3.5 L) at 0° C. was added portionwise pyridinium dichromate (794 g, 2110 mmol). To the mixture under nitrogen atmosphere was added dropwise tert-butyl hydroperoxide (355 mL, 2130 mmol) over a period of 10 min. The reaction mixture was warmed to 27° C. and was then stirred at that temperature for 48 h. Progress of the reaction was monitored by TLC (SiO$_2$, 30% Acetone/pet, Rf=0.4, UV-active). The reaction mixture was filtered, and the filter cake was extracted with EtOAc (1000 mL). The filtrate was washed with saturated aq. Na$_2$S$_2$O$_3$ (2×500 mL); saturated aq. FeSO$_4$ (300 mL); and then brine (500 mL). The organic layer was dried over anhydrous Na$_2$SO$_4$, filtered and concentrated under reduced pressure to obtain the crude title compound (150 g).

Preparation of ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate

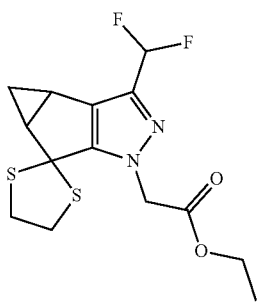 [SMILES: CCOC(=O)Cn1nc(C(F)F)c2c1C1(SCCS1)C1CC21]

To a stirred solution of ethyl 2-(3-(difluoromethyl)-5-oxo-3b,4,4a,5-tetrahydro-1H-cyclopropa[3,4]cyclopenta[1,2-c]pyrazol-1-yl)acetate (75 g, 269 mmol) in DCM (1500 mL) at 27° C. under nitrogen atmosphere was added ethane-1,2-dithiol (43.0 mL, 511 mmol) followed by the addition of boron trifluoride acetic acid (72.6 mL, 511 mmol). The solution was stirred for 16 h. Progress of the reaction was monitored by TLC (SiO$_2$, 20% Acetone/Pet, Rf=0.35, UV-Active). After completion, the reaction mixture was cooled to 0° C. and quenched via the addition of aq. saturated NaHCO$_3$(500 mL). The mixture was extracted with DCM (2×1000 mL). The combined organics were washed with brine (1000 mL), dried over anhydrous Na$_2$SO$_4$, filtered and concentrated under reduced pressure to obtain a brown liquid. This material was subjected to silica gel column chromatography (Pet.:EtOAc 95:5→90:10) to afford ethyl 2-(3-(difluoromethyl)-4,4a-dihydrospiro[cyclopropa[3,4]cyclopenta[1,2-c]pyrazole-5,2'-[1,3]dithiolane]-1(3bH)-yl)acetate as an off-white solid, 80 g (74%). $^1$H-NMR (400 MHz, CDCl$_3$) δ=6.61 (t, J=55.2 Hz, 1H), 5.00-4.85 (m, 2H), 4.29-4.19 (m, 2H), 3.55-3.46 (m, 4H), 2.63-2.53 (m, 1H), 2.49-2.38 (m, 1H), 1.30-1.24 (m, 4H), 0.65-0.60 (m, 1H). LCMS M+H=346.9.

Preparation of ethyl 2-(3-(difluoromethyl)-5,5-difluoro-3b,4,4a,5-tetrahydro-1H-cyclopropa[3,4]cyclopenta[1,2-c]pyrazol-1-yl)acetate

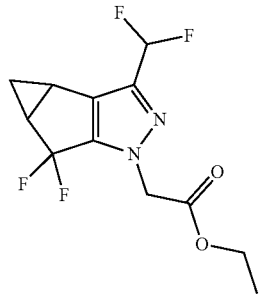 [SMILES: CCOC(=O)Cn1nc(C(F)F)c2c1C(F)(F)C1CC21]

To a stirred solution of 1,3-dibromo-5,5-dimethylimidazolidine-2,4-dione (26.3 g, 92 mmol) in DCM (20 mL) at −70° C. under N2 atmosphere was added HF-pyridine (2.460 g, 24.83 mmol). The solution was for 30 min. To the solution was added a solution of ethyl 2-(3-(difluoromethyl)-4,4a-dihydrospiro[cyclopropa[3,4]cyclopenta[1,2-c]pyrazole-5,2'-1,3]dithiolane]-1(3bH)-yl)acetate (10 g, 25 mmol) in DCM (20 mL). The reaction mixture was allowed to warm to −40° C. and then was stirred at that temperature for 1 h. Progress of the reaction was monitored by TLC (SiO$_2$, 30% EtOAc/Pet, Rf=0.3, UV in-active). The reaction mixture was quenched via the addition of aq. sat. NaHCO$_3$ (200 mL). The mixture was warmed to room temperature and was then extracted with EtOAc (2×100 mL). The combined organics were washed with brine (50 mL); dried over anhydrous Na$_2$SO$_4$; filtered; and were concentrated under reduced pressure to afford a brown solid. This material was subjected to silica gel column chromatography (Pet.: EtOAc 100:0→75-25) to afford ethyl 2-(3-(difluoromethyl)-5,5-difluoro-3b,4,4a,5-tetrahydro-1H-cyclopropa[3,4]cyclopenta[1,2-c]pyrazol-1-yl)acetate as a pale yellow solid, 8.5 g (91%). $^1$H NMR (400 MHz, CDCl$_3$) δ=6.62 (t, J=55.2 Hz, 1H), 4.82 (s, 2H), 4.30-4.18 (m, 2H), 2.51-2.37 (m, 2H), 1.42-1.35 (m, 1H), 1.31-1.23 (m, 3H), 1.14-1.08 (m, 1H). LCMS M+H=293.07.

Preparation of 2-(3-(difluoromethyl)-5,5-difluoro-3b, 4,4a,5-tetrahydro-1H-cyclopropa[3,4]cyclopenta [1,2-c]pyrazol-1-yl)acetic acid

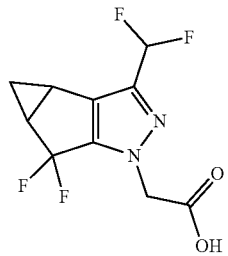 [SMILES: O=C(O)Cn1nc(C(F)F)c2c1C(F)(F)C1CC21]

To a stirred solution of ethyl 2-(3-(difluoromethyl)-5,5-difluoro-3b,4,4a,5-tetrahydro-1H-cyclopropa[3,4]cyclopenta[1,2-c]pyrazol-1-yl)acetate (15 g, 50 mmol) in THF (17 mL) and MeOH (66 mL) at 0° C. under N2 atmosphere was added a solution of LiOH (1.788 g, 74.7 mmol) in water (66 mL). The reaction mixture was allowed to warm to 27° C. and was then stirred for 3 h at that temperature. Progress of the reaction was monitored by TLC (SiO₂, 5% MeOH/DCM, Rf=0.2, UV Active). After completion, the reaction mixture was concentrated under reduced pressure; diluted with water (50 mL); and washed with EtOAc (2×250 mL) to remove impurities. The aqueous layer was adjusted to pH 2-3 using aq. HCl (1M), then was extracted with EtOAc (3×1000 mL). The combined organics were dried over anhydrous Na₂SO₄; filtered; and concentrated under reduced pressure to afford 2-(3-(difluoromethyl)-5,5-difluoro-3b,4,4a,5-tetrahydro-1H-cyclopropa[3,4]cyclopenta[1,2-c]pyrazol-1-yl)acetic acid as an off white solid, 14 g (98%). LCMS M+H=265.15.

Separation Affording 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid and 2-((3bR,4a5)-3-(difluoromethyl)-5,5-difluoro-3b,4,4a,5-tetrahydro-1H-cyclopropa[3,4]cyclopenta[1,2-c]pyrazol-1-yl)acetic acid

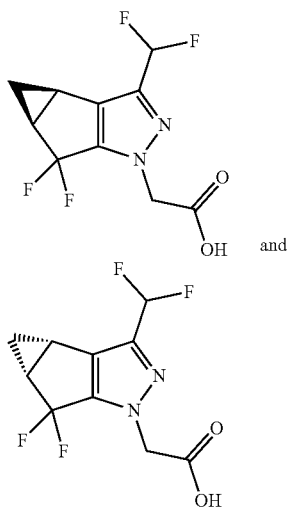

and 2-(3-(difluoromethyl)-5,5-difluoro-3b,4,4a,5-tetrahydro-1H-cyclopropa[3,4]cyclopenta[1,2-c]pyrazol-1-yl)acetic acid (5.5 g) was dissolved in isopropanol (20 mL). The solution was subjected portion-wise to SFC chiral separation as follows: Instrument=Thar 80; column=Chiralpak IC 30×250 mm, 5 micron; solvent A=super critical CO₂; solvent B=isopropanol with 0.5% isopropylamine (v/v); eluent composition=70% A:30% B; flow-rate=65 g/min; back-pressure=100 bar; temperature=30° C.; injection volume=2.5 mL; detection=220 nm. 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid was collected as peak eluting from 7.5 min. to 14 min; 2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetic acid was collected as a peak eluting from 2.7 min. to 5.8 min. For each enantiomer, the resulting solution was concentrated under reduced pressure and the resulting solids were dissolved in EtOAc, then twice washed with aq. citric acid (1M) followed by water followed by brine. The organic solution was dried over Na₂SO₄; filtered; then concentrated in vacuo to afford the separated enantiomer in 80-90% recovery.

Preparation of 3-bromo-6-chloro-2-fluorobenzonitrile

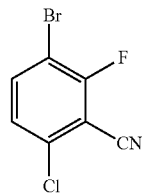 [SMILES: N#Cc1c(Cl)ccc(Br)c1F]

To a stirred solution of 3-bromo-6-chloro-2-fluorobenzaldehyde (210.0 g, 0.89 mol, 1.0 equiv.) in water (2.1 L) at room temperature was added hydroxylamine-O-sulfonic acid (175.15 g, 1.55 mol, 1.75 equiv.). The reaction mixture was heated to 50° C. and stirred for 18 h). The mixture was cooled to room temperature and stirred for 1-1.5 h. The solids were isolated via filtration and were then washed with water. The wet solid was dried under vacuum at 50° C. for 12-15 h to afford 3-bromo-6-chloro-2-fluorobenzaldehyde, 190.0 g (91%).

Preparation of 7-bromo-4-chloro-1-methyl-1H-indazol-3-amine

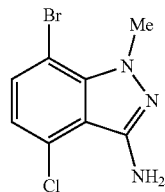 [SMILES: Cn1nc(N)c2c(Cl)ccc(Br)c21]

To a solution of 3-bromo-6-chloro-2-fluorobenzonitrile (360.0 g, 1.55 mol, 1.0 equiv.) in ethanol (1.08 L) was added methylhydrazine sulphate (1.11 kg, 7.73 mol, 5.0 equiv.) followed by the addition of triethylamine (1.3 L, 9.3 mol, 6.0 equiv.) at 25-35° C. The reaction mixture was heated to 110° C. and maintained for 15 h (the reaction was monitored by TLC). After completion of the reaction the mixture was cooled to room temperature. Water (3.0 L) was added and the mixture was stirred for 1 h at room temperature. The solids were isolated via filtration and were washed with water. The wet solid was dried under vacuum at 50° C. for 12-15 hours. The crude solid was purified by column chromatography (10% EA/hexanes to 40% EA/Hexanes) to afford the product as a pale yellow solid. Yield: 185.0 g (46.0%).

Preparation of N-(7-bromo-4-chloro-1-methyl-1H-indazol-3-yl)methanesulfonamide

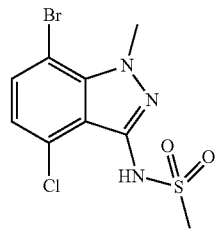 [SMILES: Cn1nc(NS(C)(=O)=O)c2c(Cl)ccc(Br)c21]

To a solution of 7-bromo-4-chloro-1-methyl-1H-indazol-3-amine (1.40 g, 5.37 mmol) in DCM (30 mL) was added Hunig's Base (3.75 mL, 21.5 mmol) and then the reaction was cooled in an ice bath and methanesulfonyl chloride (1.26 mL, 16.1 mmol) was added. The reaction mixture was stirred at this temperature for 1 h (precipitate formed). Mixture was then diluted with dichloromethane (100 mL) and washed with water, 1 M HCl and brine, dried (Na$_2$SO$_4$), filtered and concentrated in vacuo. The residue was taken up in EtOH (30 ml) and 10 ml of 20% aq. NaOH. The resulted mixture heated with a heat gun until it became a homogenous solution and stirred at rt for 30 min. The mixture was diluted with water (80 mL) and acidified with 1 N HCl (60 mL). The precipitate was filtered, washed with water, and dried in vacuo to afford the title product (1.5 g) as an off-white solid. $^1$H NMR (500 MHz, CDCl$_3$) δ 7.48 (d, J=7.9 Hz, 1H), 7.24 (br s, 1H), 6.95 (d, J=7.9 Hz, 1H), 4.38 (s, 3H), 3.42 (s, 3H). LC/MS (M+H)+=337.80.

Preparation of N-(7-bromo-4-chloro-1-methyl-1H-indazol-3-yl)-N-(4-methoxybenzyl)methanesulfonamide

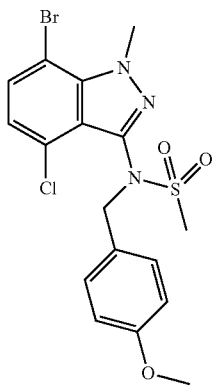 [SMILES: COc1ccc(CN(c2nn(C)c3c(Br)ccc(Cl)c23)S(C)(=O)=O)cc1]

To a mixture of N-(7-bromo-4-chloro-1-methyl-1H-indazol-3-yl)methanesulfonamide (1.3 g, 3.84 mmol) and 1-(chloromethyl)-4-methoxybenzene (0.625 mL, 4.61 mmol) in DMF (30 mL) was added cesium carbonate (1.626 g, 4.99 mmol) and the mixture was heated at 80° C. for 2 h. The mixture was poured into water (100 mL) and extracted with EtOAc (50 ml, 2×). The combined organic layer was washed with brine, dried over MgSO$_4$, filtered and concentrated in vacuo. The residue was purified by Bioateg (0~35% EtOAc-hexanes) to afford the title product (1.5 g) as a white foam. $^1$H NMR (500 MHz, CDCl$_3$) δ 7.44 (d, J=7.9 Hz, 1H), 7.31 (d, J=8.5 Hz, 2H), 6.99 (d, J=7.9 Hz, 1H), 6.84 (d, =8.5 Hz, 2H), 4.99 (br s, 1H), 4.76 (br s, 1H), 4.40 (s, 3H), 3.80 (s, 3H), 3.01 (s, 3H).

Preparation of N-(7-amino-4-chloro-1-methyl-1H-indazol-3-yl)-N-(4-methoxybenzyl)methanesulfonamide

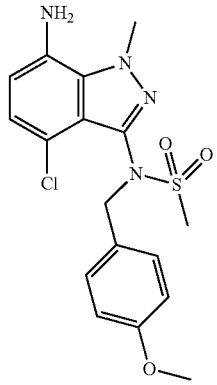 [SMILES: COc1ccc(CN(c2nn(C)c3c(N)ccc(Cl)c23)S(C)(=O)=O)cc1]

Following the reference: Andersen, Jacob et al, Synlett 2005 (14), 2209-2213. To a mixture of N-(7-bromo-4-chloro-1-methyl-1H-indazol-3-yl)-N-(4-methoxybenzyl) methane sulfonamide (600.0 mg, 1.308 mmol), copper(I) iodide (49.8 mg, 0.262 mmol), sodium ascorbate (518 mg, 2.62 mmol) and (1R,2R)—N1,N2-dimethylcyclohexane-1, 2-diamine (46.5 mg, 0.327 mmol) in NMP (10 mL) was added a solution of sodium azide (255 mg, 3.92 mmol) in Water (2.0 mL). The mixture was then sealed and heated in a microwave system at 120° C. for 2.5 h. The mixture was then filtered through a pad of Celite and the pad was washed with EtOAc. The filtrate was poured into water (100 mL) and extracted with EtOAc (50 ml, 2×). The combined organic layer was washed with brine, dried over MgSO$_4$, filtered and evaporated in vacuo. The residue was purified by Biotage (5-100% EtOAc/hexanes) to afford the title product (400 mg) as an off-white solid. $^1$H NMR (400 MHz, CDCl$_3$) δ 7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS (M+H)+=395.00.

Preparation of 2-amino-6-(benzyloxy)nicotinic acid

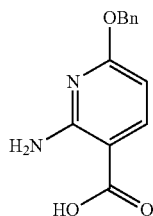

A solution of 2-amino-6-chloronicotinic acid (5 g, 29 mmol) and potassium tert-butoxide (9.75 g, 87 mmol) in benzyl alcohol (97 mL) was heated to 120° C. for 3 h. After cooling to ambient temperature, the very dark reaction mixture was added to water and washed with ether (×3). The aqueous layer was then acidified with 0.5 M citric acid. The tan precipitate filtered to provide the product (4.4 g, 62%) which was used in the next reaction without further purification. $^1$H NMR (500 MHz, DMSO-d6) δ 12.40 (br s, 1H), 7.94 (d, J=8.55 Hz, 1H), 7.06-7.52 (m, 5H), 6.04 (d, J=8.24 Hz, 1H), 5.33 (s, 2H). LC/MS: m/z=245.15 [M+1]+.

Preparation of N-[(6P)-7-{2-[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N-[(4-methoxyphenyl)methyl]methanesulfonamide Scheme:

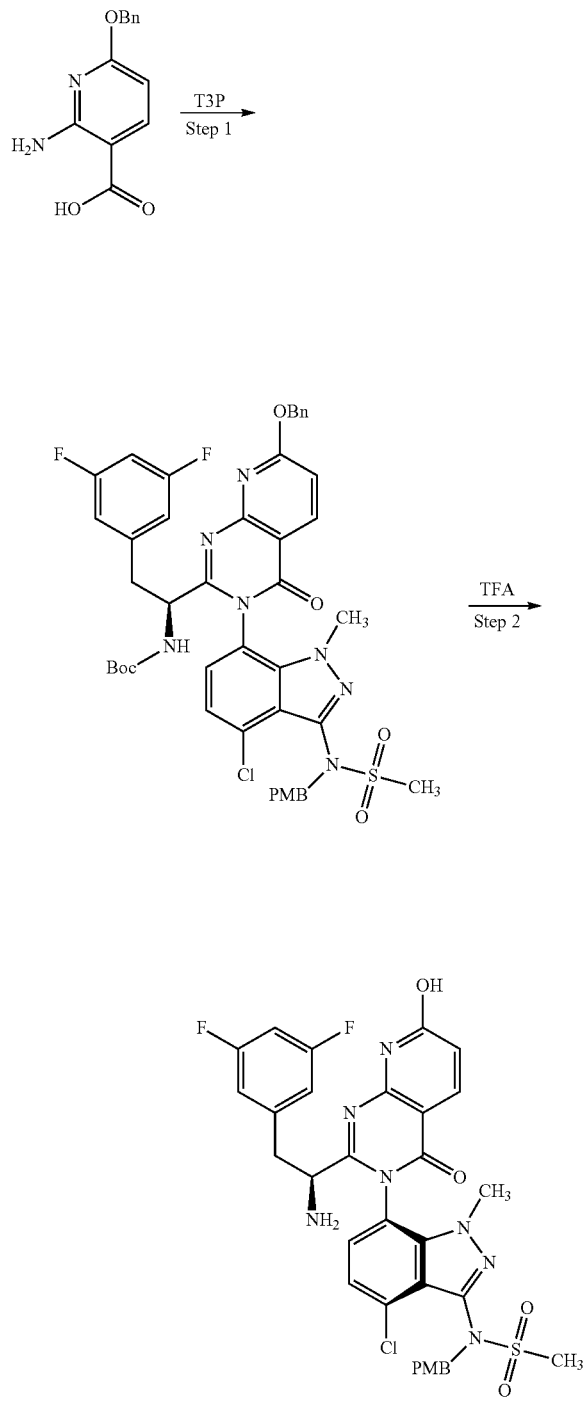

Step 1:

To a suspension of (S)-2-((tert-butoxycarbonyl)amino)-3-(3,5-difluorophenyl)propanoic acid (5.49 g, 18.23 mmol) and 2-amino-6-(benzyloxy)nicotinic acid (4.45 g, 18.23 mmol) in acetonitrile (92 mL) (yellow solution) at −25° C. was added pyridine (9.83 mL, 122 mmol) followed by 2,4,6-tripropyl-1,3,5,2,4,6-trioxatriphosphinane 2,4,6-trioxide ("T3P", 45.2 ml, 76 mmol). The reaction mixture (became a clear solution after T3P addition) was stirred at −25° C. to 10° C. over 4.5 h, then N-(7-amino-4-chloro-1-methyl-1H-indazol-3-yl)-N-(4-methoxybenzyl)methanesulfonamide (6 g, 15.19 mmol) was added and the mixture was stirred for 18 h while warming to rt. The reaction mixture was diluted with ethyl acetate, washed with 1N NaOH, then water, then 0.5 M citric acid, then water, then dried over Na$_2$SO$_4$ and concentrated in vacuo. The resulting residue was purified on silica (330 g RediSep Gold column) using 0-60% ethyl acetate in hexanes over 15 CV, then holding at 60% EtOAc for 10 CV. The desired fractions were pooled and concentrated to afford a pale yellow solid (8.1 g, 9.14 mmol, 60.1% yield), a mixture of tert-butyl N-[(1S)-1-[(3P,3P)-7-(benzyloxy)-3-(4-chloro-3-{N-[(4-methoxyphenyl)methyl]methanesulfonamido}-1-methyl-1H-indazol-7-yl)-4-oxo-3H,4H-pyrido[2,3-d]pyrimidin-2-yl]-2-(3,5-difluorophenyl)ethyl]carbamate (major) and tert-butyl N-[(1S)-1-[(3M,3M)-7-(benzyloxy)-3-(4-chloro-3-{N4(4-methoxyphenyl)methyl)methanesulfonamido}-1-methyl-1H-indazol-7-yl)-4-oxo-3H,4H-pyrido[2,3-d]pyrimidin-2-yl]-2-(3,5-difluorophenyl)ethyl]carbamate (minor). LC/MS: m/z=886.25 [M+1]$^+$.

Step 2:

TFA (21.1 mL, 274 mmol) was added to a solution of tert-butyl (S)-(1-(7-(benzyloxy)-3-(4-chloro-3-(N-(4-methoxybenzyl)methylsulfonamido)-1-methyl-1H-indazol-7-yl)-4-oxo-3,4-dihydropyrido[2,3-d]pyrimidin-2-yl)-2-(3,5-difluorophenyl)ethyl)carbamate (Product from Step 1, 8.1 g, 9.14 mmol) in dichloromethane (45.7 mL). The mixture was stirred at rt for 2 h. The resultant pale-yellow solution was concentrated. The residue was taken up in ethyl acetate, then washed three times with 1 N NaOH, then dried over Na$_2$SO$_4$ and then concentrated in vacuo to afford an oily residue. The residue was purified on silica gel (330 g RediSep Gold column) by a gradient method of Solvent A:Solvent B 65:35→0:100 (2 CV), then 0:100 (9 CV); Solvent A=hexanes; Solvent B=9:9:2 hexanes:ethyl acetate: MeOH. The first eluting isomer (major) was collected and concentrated in vacuo to afford N-[(6P)-7-{2[(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-yl]-N4(4-methoxyphenyl)methyl]methanesulfonamide (4.1 g, 5.89 mmol, 64.5% yield). $^1$H NMR (500 MHz, DMSO-d6) δ7.86-7.98 (m, 1H) 7.15-7.37 (m, 4H) 6.97-7.06 (m, 1H) 6.70-6.89 (m, 4H) 6.40-6.48 (m, 1H) 4.70-4.88 (m, 2H) 3.41-3.81 (m, 7H) 3.20-3.28 (m, 1H) 3.08-3.12 (m, 3H) 2.71-2.79 (m, 1H) 1.69-2.00 (m, 2H). LC/MS: m/z=696.20 [M+1]$^+$.

Preparation of N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Preparation of Example 1: N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

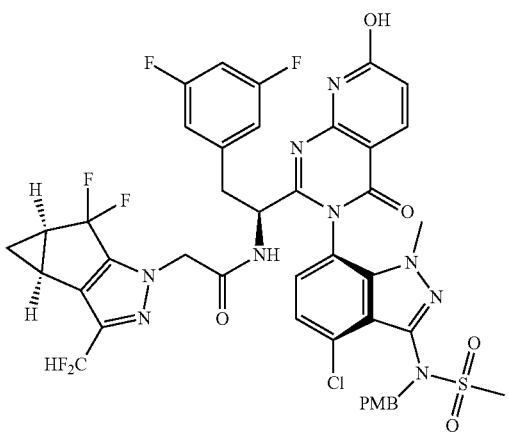

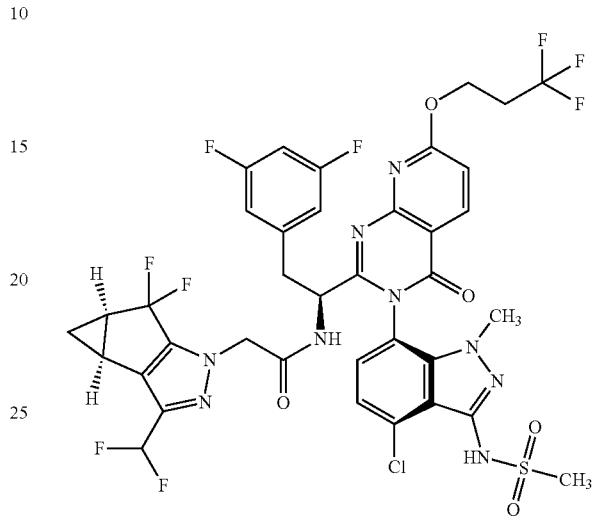

To a stirred solution of N-[(6P)-7-{24(1S)-1-amino-2-(3,5-difluorophenyl)ethyl]-7-hydroxy-4-oxo-3H,4H-pyrido[2,3-d]pyrimidin-3-yl}-4-chloro-1-methyl-1H-indazol-3-A-N-[(4-methoxyphenyl)methyl]methanesulfonamide (0.926 g, 1.330 mmol) in DMF (13 ml) was added 2-((3bS,4aR)-3-(difluoromethyl)-5,5-difluoro-3b,4,4a,5-tetra hydro-1H-cyclopropa[3,4]cyclopenta[1,2-c]pyrazol-1-yl)acetic acid (0.351 g, 1.330 mmol), 2-(3H-[1,2,3]triazolo[4,5-b]pyridin-3-yl)-1,1,3,3-tetramethylisouronium hexafluorophosphate (V) ("HATU", 0.531 g, 1.397 mmol), and DIPEA (0.581 ml, 3.33 mmol). The reaction mixture was stirred for 2 h after which the reaction mixture was diluted with water and extracted with ethyl acetate. The combined EtOAc extractions were washed with brine, dried over $Na_2SO_4$, and concentrated in vacuo. The crude product was purified via silica gel flash chromatography using 10-100% ethyl acetate in hexanes to provide N—((S)-1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.1 g, 88%) as an off-white foamy solid. LC/MS: m/z=942.25 [M+1]+.

A solution of diisopropyl (E)-diazene-1,2-dicarboxylate ("DIAD", 0.125 ml, 0.637 mmol) in THF (0.2 mL) was added dropwise to a mixture of N-(1-((3P)-3-(4-chloro-3-(N-(4-methoxybenzyl)methylsulfonamido)-1-methyl-1H-indazol-7-yl)-7-hydroxy-4-oxo-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.2 g, 0.212 mmol)), 3,3,3-trifluoropropan-1-ol (0.073 g, 0.637 mmol) and triphenylphosphine (0.178 g, 0.679 mmol) in Tetrahydrofuran (2.1 mL) at rt. The reaction mixture was stirred for 18 h at rt and then was concentrated in vacuo. The residue was purified on silica gel (24 g RediSep Gold column) using a gradient of 0-60% ethyl acetate in hexanes over 15 CV, and then holding at 60% ethyl acetate in hexanes for 5 CV. Fractions containing the pure product were pooled and then concentrated to give a yellow solid. This solid was taken up in DCM (1 mL):TFA (0.5 mL); the solution was cooled to 0° C.; and to the solution was added triflic acid (0.057 mL, 0.637 mmol). The mixture was stirred for 1 h and then concentrated in vacuo. The residue was taken up in ethyl acetate; washed with 1 N NaOH; washed with 0.5M citric acid; dried over $Na_2SO_4$; filtered; and then was concentrated in vacuo. The residue was subjected to silica gel chromatography (24 g RediSep Gold column) using 0-60% ethyl acetate in hexanes over 20 CV, then at 60% ethyl acetate for 10 CV. Fractions containing the pure product were pooled and then concentrated in vacuo to give N-(1-((6P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (0.078 g, 0.081 mmol, 38.0% yield) as a brown solid. $^1$H NMR (500 MHz, METHANOL-$d_4$) δ ppm 8.46-8.53 (m, 1H) 7.28-7.34 (m, 1H) 7.19-7.24 (m, 1H) 7.03-7.09 (m, 1H) 6.53-6.81 (m, 4H) 4.80 (dd, J=5.96, 2.98

Hz, 3H) 4.49-4.62 (m, 2H) 3.58-3.62 (m, 3H) 3.40-3.49 (m, 1H) 3.22-3.24 (m, 3H) 3.06-3.14 (m, 1H) 2.80-2.89 (m, 2H) 2.37-2.44 (m, 2H) 1.32-1.37 (m, 1H) 0.96-1.01 (m, 1H). LCMS Analysis Method: Column=Acquity UPLC BEH C18, 2.1×100 mm, 1.7 μm particles; Injection Volume=5.00 μL; Flowrate=0.80 mL/min; Solvent A=95:5 Water:MeCN w/0.1% v/v formic acid; Solvent B=5:95 Water:MeCN w/0.1% v/v formic acid; Elution profile=Start % B: 0, End % B: 100, Gradient Time: 3.5 min. then hold at 100% B for 1 min.; Detection wavelength 1=220 nm, wavelength 2=254 nm. LCMS retention time=3.097 min; m/z=918.05 [M+1]+.

Alternate Preparation of N-(7-amino-4-chloro-1-methyl-1H-indazol-3-yl)-N-(4-methoxybenzyl)methanesulfonamide

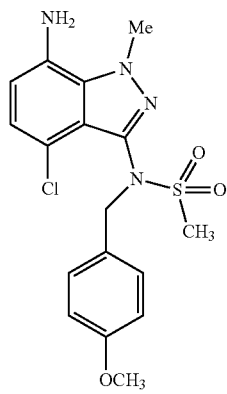 [SMILES: COc1ccc(CN(c2nn(C)c3c(N)ccc(Cl)c23)S(C)(=O)=O)cc1]

Synthesis Scheme:

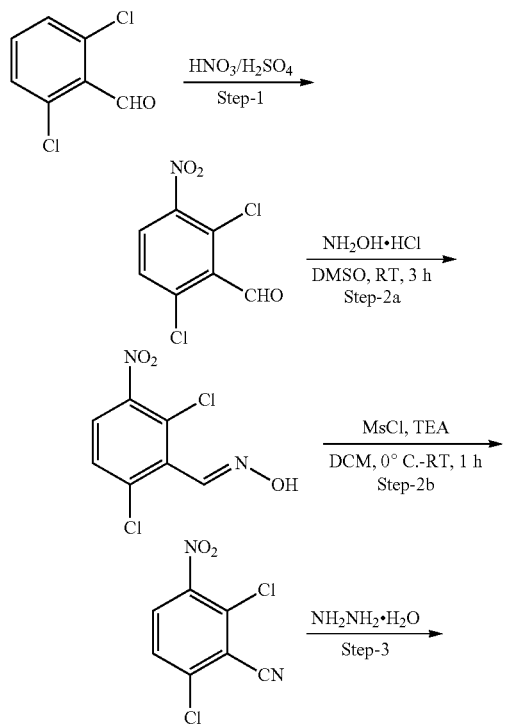

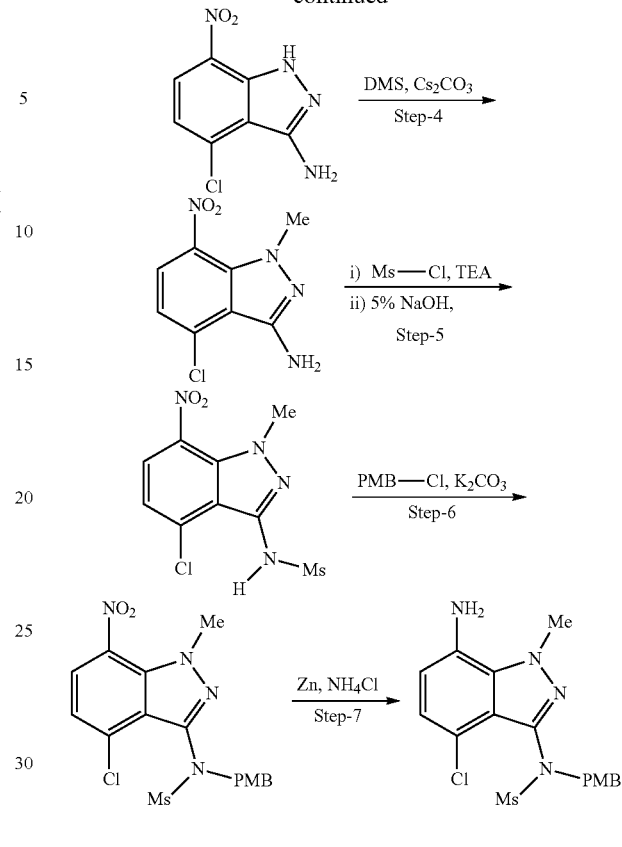

Step 1: Preparation of 2,6-dichloro-3-nitrobenzaldehyde

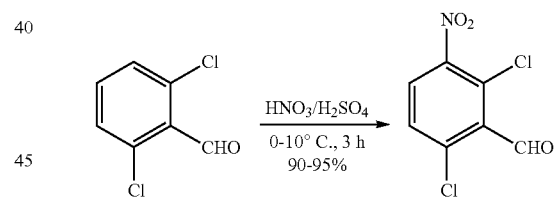

To a solution of sulfuric acid (H$_2$SO$_4$) (5.63 L, 4.5 V) in a round-bottom flask at 0-5° C. was added 2,6-dichlorobenzaldehyde (1.25 kg, 7.10 mol, 1.0 equiv.) in portions at below 15° C. The reaction mass was stirred at 0-5° C. for 30 min. A solution of freshly prepared nitration mixture [Prepared from Conc. H$_2$SO$_4$ (0.425 L, 0.34 V) and 70% HNO3 (0.85 kg, 13.49 mol, 1.30 equiv.) at 0° C.] was added to the above reaction mixture at below 10° C. [Note: Reaction is slightly exothermic (3-6° C.); so that addition is preferred at lower temperature]. The reaction mixture was stirred at 5-10° C. for 2-3 h. After completion of the reaction (monitored by TLC), it was quenched with ice cold water (18.75 L, 15 V) at below 25° C. Then the reaction mass was allowed warm to room temperature and stirred for 2 h. The solids were isolated by filtration and then were washed with water (2.5 L, 2.0 V). Bulk residual water was removed from the solids by maintaining vacuum filtration for 60-90 min. The crude wet solid was initially dried under air atmosphere; then in a hot air oven at 50-55° C. for 10-12 h (until moisture content is not more than 5.0%) to get the dried title product, 2,6-dichloro-3-nitrobenzaldehyde (1.44 kg, 92% yield) as a yellow solid. $^1$H NMR (400 MHz, CDCl$_3$): δ10.44 (s, 1H), 7.88 (d, J=8.4 Hz, 1H), 7.56 (d, J=8.8 Hz, 1H).

Step 2: Preparation of
2,6-dichloro-3-nitrobenzonitrile

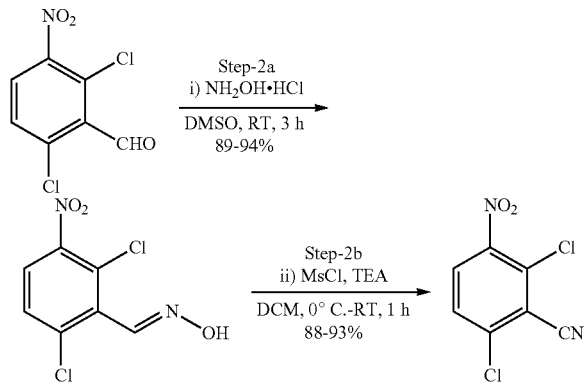

(Step-2a) To a solution of DMSO (5.9 L, 5.0 V)) in a round-bottom flask was added 2,6-dichloro-3-nitrobenzaldehyde (1.17 kg, 5.31 mol, 1.0 equiv.) at room temperature. After being stirred for 30 min at room temperature, hydroxylamine hydrochloride (0.63 kg, 9.04 mol, 1.70 equiv.) was added and the reaction mass was stirred at room temperature for 3 h. After completion of the reaction (monitored by TLC), the reaction mass was quenched by the addition of ice-cold water (18.0 L, 15.0 V) added at a rate sufficient to maintain the temperature below 30° C. (Observation: Solids formed upon water addition). The reaction mass was stirred at room temperature for 60-90 min. The solids were isolated by filtration; washed with water (2.5 L, 2.0 V); followed by washing with a mixture of acetone and hexanes (6.0 L, 1:1 ratio). Bulk residual water was removed from the solids by maintaining vacuum filtration for 60-90 min. The wet solid was initially air dried and then finally dried in a hot air oven at 50-55° C. for 10-12 h (until moisture content was not more than 1.0%) to get the dried target product, 2,6-dichloro-3-nitrobenzaldehyde oxime (1.22 kg, 92% yield) as an off-white solid. The crude product (which contains 10-20% of 2,6-dichloro-3-nitrobenzonitrile) was used directly in the next step without further purification.

(Step-2b) To a stirred solution of the crude oxime (preparation described above, 1.13 kg, 4.80 mol, 1.0 equiv.) in DCM (9.04 L, 8.0 V) at 0-5° C. was added triethylamine ("TEA", 1.02 kg, 10.09 mol, 2.1 equiv.). After being stirred for 5 min, methanesulfonyl chloride (0.60 kg, 5.29 mol, 1.1 equiv.) was added (Observation: An exotherm is noted during the addition) slowly at 15° C. Then the reaction mass was stirred at room temperature for 30-45 min. After completion of the reaction (progress of reaction was monitored by TLC; mobile phase: 20% ethyl acetate in hexanes), the reaction mass was diluted with water (6.78 L, 6.0 V); the organic layer was separated; and the aqueous layer was extracted with DCM (3.4 L, 3.0 V). The combined organic layers were washed with brine (5.65 L, 5.0 V); dried over Na$_2$SO$_4$; and concentrated under vacuum. The resulting crude solids were triturated with hexanes (4.50 L, 4.0 V) at room temperature. The wet material was dried in a hot air oven at 50-55° C. for 5-6 h to get the dried product, 2,6-dichloro-3-nitrobenzonitrile (0.95 kg, 91% yield) as a yellow solid. $^1$H NMR (400 MHz, CDCl$_3$): δ8.07 (d, J=8.8 Hz, 1H), 7.63 (d, J=8.8 Hz, 1H).

Step 3: Preparation of
4-chloro-7-nitro-1H-indazol-3-amine

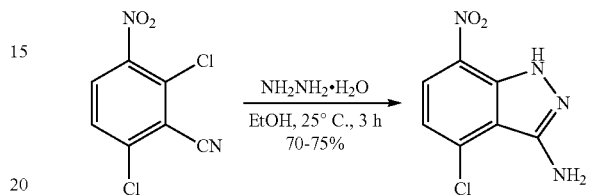

To a stirred solution of 2,6-dichloro-3-nitrobenzonitrile (750.0 g, 3.45 mol, 1.0 equiv.) in ethanol (7.5 L, 10.0 V) at 15-20° C. was slowly added hydrazine hydrate (519.0 g, 10.36 mol, 3.0 equiv.) while maintaining the reaction mass below 25° C. (Observation: Addition is slightly exothermic and solid formation will begin upon addition). The reaction mixture temperature was slowly raised to room temperature and then the mixture was stirred for 3 h (Observation: the quantity of solids will increase during this time). After completion of the reaction (monitored by TLC), the mixture was diluted with water (7.5 L, 10.0 V) and further stirred for 1 h at room temperature. The solids were isolated via filtration and then were washed with water (2.25 L, 3.0 V). The wet solid was washed with a 1:1 ratio mixture of acetone (1.875 L, 2.5 V) and hexanes (1.875 L, 2.5 V). Bulk residual water was removed from the solids by maintaining vacuum filtration for 60-90 min. The wet solid was finally dried in a hot air oven for 7-8 h at 50° C. (until moisture content reaches below 1.5%) to get the dried product, 4-chloro-7-nitro-1H-indazol-3-amine (549.0 g, 75% yield) as a brick red-colored solid. $^1$H NMR (400 MHz, CDCl$_3$): δ10.36 (bs, 1H), 8.20 (d, J=8.4 Hz, 1H), 7.07 (d, J=8.40 Hz, 1H), 4.73 (bs, 2H).

Step 4: Preparation of
4-chloro-1-methyl-7-nitro-1H-indazol-3-amine

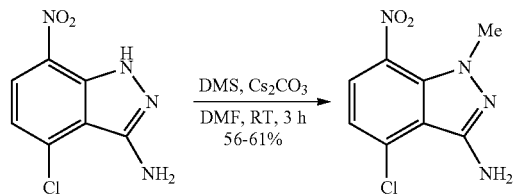 [SMILES: Nc1n[nH]c2c([N+](=O)[O-])ccc(Cl)c12 ; Cn1nc(N)c2c(Cl)ccc([N+](=O)[O-])c21]

To a stirred solution of 4-chloro-7-nitro-1H-indazol-3-amine (500 g, 0.42 mol, 1.0 equiv.) in DMF (5.0 L, 10.0 V) at 5-10° C. was slowly added cesium carbonate (Cs$_2$CO$_3$) (1.91 kg, 5.88 mol, 2.5 equiv.) while maintaining the reaction mass below 10° C. After being stirred for 5-10 min, dimethyl sulphate (326.3 g, 2.59 mol, 1.1 equiv.) was added while maintaining the reaction mass below 10° C. (Note: Slow addition is preferred for obtaining more favorable regio-selectivity). Then, the reaction temperature was slowly raised to room temperature and stirring was continued an additional 2 h at the same temperature. After completion of the reaction (monitored by TLC), the reaction mass was quenched by the addition of ice-cold water (15.0 L, 30.0 V) and the resulting mixture was then stirred for 6-8 h at room temperature. The solids were isolated via filtration and were then washed with water (1.5 L, 3.0 V). The wet solid was washed with IPA (1.5 L, 3.0 V) followed by hexanes (1.0 L, 2.0 V). Bulk residual water was removed from the solids by maintaining vacuum filtration for 60-90 min. The wet solid was dried in a hot air oven for 7-8 h at 50° C. (until moisture content is below 1.0%). The isolated material, 4-chloro-1-methyl-7-nitro-1H-indazol-3-amine (319.0 g, 60% yield), was used in the next step without further purification. $^1$H NMR (400 MHz, CDCl$_3$): δ7.97 (d, J=8.32 Hz, 1H), 6.97 (d, J=8.24 Hz, 1H), 4.63 (bs, 2H), 3.96 (s, 3H).

Step 5: Preparation of N-(4-chloro-1-methyl-7-nitro-1H-indazol-3-yl)methanesulfonamide

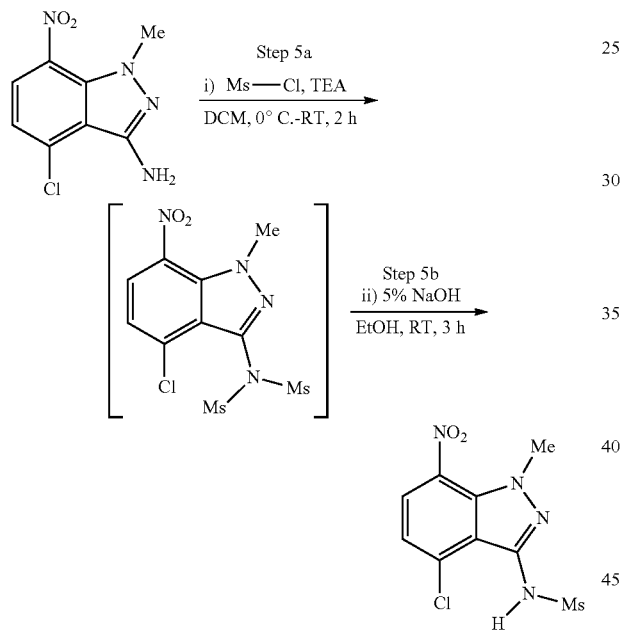

(Step 5a) To a solution of 4-chloro-1-methyl-7-nitro-1H-indazol-3-amine (625.0 g, 2.76 mol, 1.0 equiv.) in DCM (6.25 L, 10.0 V) at 0-5° C. was added triethylamine (TEA) (837.0 g, 8.27 mol, 3.0 equiv.); followed by the addition of 4-dimethylaminopyridine (DMAP) (20.60 g, 0.165 mol, 0.06 equiv.). The reaction mass was stirred for 5-10 min., then methanesulfonyl chloride (MsCl) (790.0 g, 6.89 mol, 2.5 equiv.) added slowly while maintaining the reaction mass below 10° C. The reaction mixture was allowed to warm to room temperature and was then stirred for 1.5-2.0 h. After completion of the reaction (monitored by TLC), the mixture was diluted with water (6.25 L, 10.0 V) and then stirred at room temperature for 15 min. The organic layer was separated, and the aqueous layer was extracted with DCM (6.25 L, 10.0 V). The combined organic layers were washed with brine (1.25 L, 2.0 V), dried over Na$_2$SO$_4$ and concentrated to get the crude solids. The solids were triturated with hexanes (1.25 L, 2.0 V) at room temperature to obtain the intermediate, N-(4-chloro-1-methyl-7-nitro-1H-indazol-3-yl)-N-(methylsulfonyl)methanesulfonamide, which was used directly in the next step.

(ii) To a stirred solution of N-(4-chloro-1-methyl-7-nitro-1H-indazol-3-yl)-N-(methylsulfonyl)methanesulfonamide (prepared above) in ethanol (10.5 L, 20.0 V) at room temperature was added slowly an aq. 5% NaOH solution (4.38 L, 7.0 V) [Note: Slow addition is preferred via dropping funnel]. The reaction mass was stirred at the same temperature for 3 h. After completion of the reaction (monitored by TLC) [Sample preparation for TLC analysis: ~1.0 ml of sample acidified with aq. 2.0 N HCl to reach the pH: 2-3, extract it with ethyl acetate and analyze the organic layer by TLC], the reaction mass was cooled to 0-5° C. and the pH was adjusted to 2-3 by the addition of aq. 2.0 N HCl (3.13 L, 5.0 V) while maintain the reaction temperature below 10° C. [Note: Precipitation occurred upon addition of HCl and increased with stirring]. The reaction mixture was warmed to room temperature and then stirred for 1.5-2.0 h. Solids obtained were isolated via filtration and were then washed with water (1.25 L, 2.0 V); followed by washing with hexanes (1.25 L, 2.0 V). Bulk residual water was removed from the solids by maintaining vacuum filtration for 60-90 min. The wet material was dried in a hot air oven at 50° C. for 6-7 h (Until the moisture content is below 1.0%) to get the dried product, N-(4-chloro-1-methyl-7-nitro-1H-indazol-3-yl)methanesulfonamide (640.0 g, 76%) as a yellow solid. $^1$H NMR (400 MHz, CDCl$_3$): δ8.05 (d, J=8.32 Hz, 1H), 7.32 (bs, 1H), 7.17 (d, J=8.28 Hz, 1H), 4.15 (s, 3H), 3.45 (s, 3H).

Step 6: Preparation of N-(4-chloro-1-methyl-7-nitro-1H-indazol-3-yl)-N-(4-methoxybenzyl)methanesulfonamide

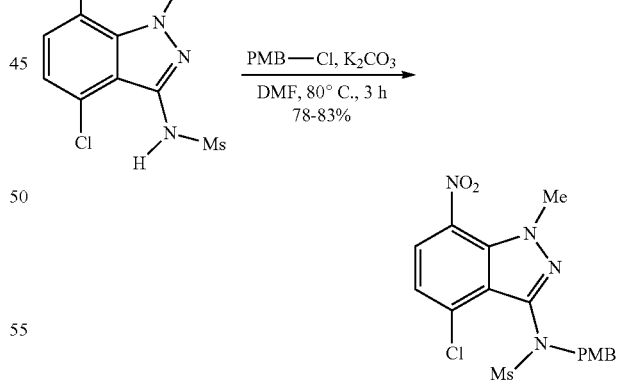

To a mixture of N-(4-chloro-1-methyl-7-nitro-1H-indazol-3-yl)methanesulfonamide (635.0 g, 2.08 mol, 1.0 equiv.) and 1-(chloromethyl)-4-methoxybenzene (359.0 g, 2.30 mol, 1.1 equiv.) in DMF (6.35 L, 10.0 V) at room temperature was added potassium carbonate (374.7 g, 2.70 mol, 1.3 equiv.). The reaction mixture was heated to 80-90° C. and maintained at that temperature for 3 h. After completion of the reaction (monitored by TLC), the mixture was poured into ice cold water (19.05 L, 30.0 V) [Note: Slow quenching with vigorous stirring is preferred to avoid clumping as the product precipitates]. The resulting solids were isolated via filtration and washed with water (1.90 L, 3.0 V); then the solids were washed with hexanes (1.27 L, 2.0 V). Bulk residual water was removed from the solids by maintaining vacuum filtration for 60-90 min. The isolated solid was dissolved in Ethyl acetate (12.7 L, 20.0 V) and charcoal was added (63.5 g). The mixture was heated to 60-70° C. and then stirred for 30-45 min. at that temperature. The mixture was filtered while still hot (40-50° C.) through a pad of Celite and the Celite pad was then extracted with ethyl acetate (3.17 L, 5.0 V). The combined filtrates were concentrated to dryness under reduced pressure at below 50° C. Ethyl acetate (0.635 L, 1.0 V) was added to the solids at room temperature. The resultant solid suspension was stirred for 30 min. The solids were isolated via filtration and then were washed with hexanes (1.27 L, 2.0 V). Residual water was removed from the solids by maintaining vacuum filtration for 45-60 min. to afford the product N-(4-chloro-1-methyl-7-nitro-1H-indazol-3-yl)-N-(4-methoxybenzyl)methane sulfonamide (705.0 g, 80% yield) as a yellow solid. $^1$H NMR (400 MHz, CDCl$_3$): δ7.99 (d, J=8.24 Hz, 1H), 7.27 (d, J=8.68 Hz, 2H), 7.19 (d, J=8.24 Hz, 1H), 6.80 (d, J=8.44 Hz, 2H), 4.95-4.76 (m, 2H), 4.17 (s, 3H), 3.76 (s, 3H), 3.01 (s, 3H).

Step 7: Preparation of N-(7-Amino-4-chloro-1-methyl-1H-indazol-3-yl)-N-(4-methoxybenzyl)methanesulfonamide

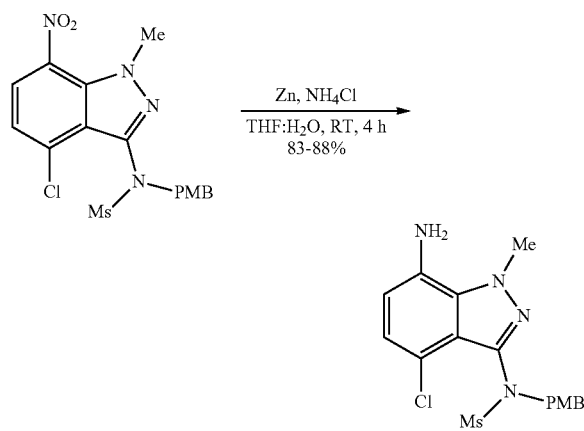

To a stirred suspension of zinc powder (540.0 g, 8.23 mol, 10.0 equiv.) in a mixture of THF (3.50 L, 10.0 V) and water (7.0 L, 20.0 V) at room temperature was added ammonium chloride (NH$_4$Cl) (449.0 g, 8.23 mol, 10.0 equiv.). To the mixture was added N-(4-chloro-1-methyl-7-nitro-1H-indazol-3-yl)-N-(4-methoxybenzyl)methanesulfonamide (350 g, 0.823 mol, 1.0 equiv.) in THF (7.0 L, 20.0 V). The reaction mixture was stirred at room temperature for 3-4 h. After completion of the reaction (monitored by in-process TLC/HPLC), the mixture was diluted with ethyl acetate (3.5 L, 10.0 V) and water (1.12 L, 2.5 V). The mixture was stirred for 15 min. The reaction mass was filtered through a pad of Celite bed washing with ethyl acetate (1.75 L, 5.0 V). The bi-phasic filtrate was collected, and the phases were separated. The aqueous layer was extracted with ethyl acetate (3.50 L, 10.0 V). The combined organic layers were washed with brine (3.50 L, 10 V), dried over Na$_2$SO$_4$, and then concentrated in vacuo to afford a crude solid. To the crude product was added MTBE (3.25 L, 10 V) and the suspension was stirred for 30 min at room temperature. The solids were isolated by filtration. Bulk residual water was removed from the solids by maintaining vacuum filtration for 30-45 min. The wet product was dried in a hot air oven (50° C.) for 2 h to afford the title product, N-(7-amino-4-chloro-1-methyl-1H-indazol-3-yl)-N-(4-methoxybenzyl)methanesulfonamide (276.0 g, 85% yield) as off-white solid. $^1$H NMR (400 MHz, CDCl$_3$): δ7.29-7.26 (m, 2H), 6.86-6.79 (m, 2H), 6.42 (d, J=7.80 Hz, 1H), 4.99-4.70 (m, 2H), 4.25 (s, 3H), 3.77 (s, 5H), 2.98 (s, 3H).

Preparation of 2-amino-6-(3,3,3-trifluoropropoxy)nicotinic acid

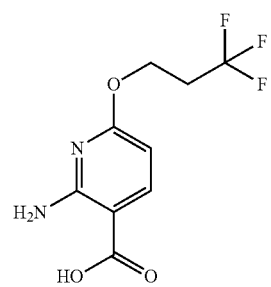 [SMILES: Nc1nc(OCCC(F)(F)F)ccc1C(=O)O]

Synthesis Scheme:

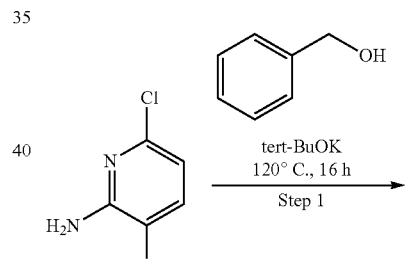

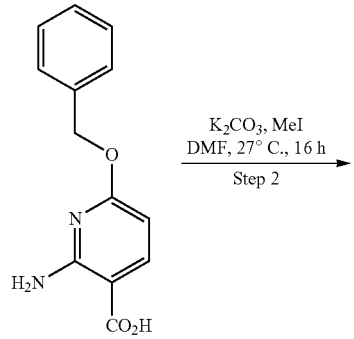

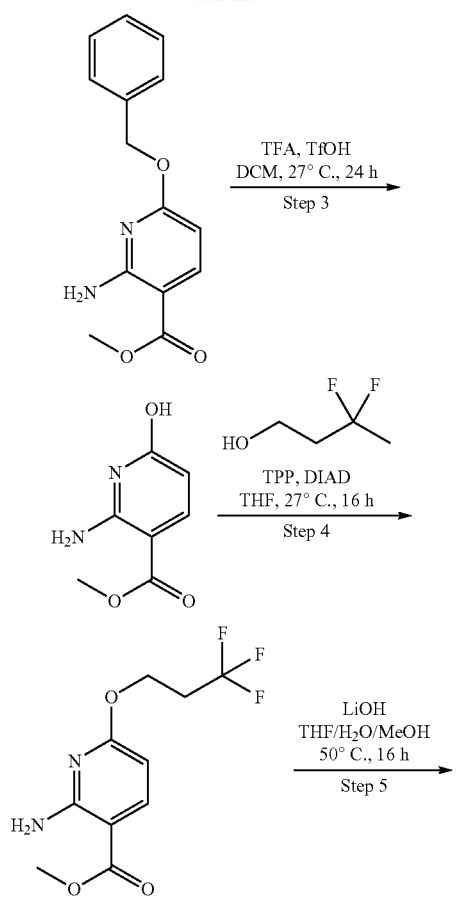

To a stirred solution of 2-amino-6-chloronicotinic acid (200 g, 1159 mmol) in benzyl alcohol (1400 mL, 13464 mmol) at 26° C. under N2 atmosphere was added potassium tert-butoxide (390 g, 3477 mmol). The reaction mixture was heated to 120° C. and stirred for 16 hr at that temperature. The progress of reaction was monitored by TLC (SiO$_2$, 10% MeOH in DCM, Rf=0.5). On completion, the reaction mixture was diluted with water (3 L) and extracted with diethyl ether (2×1000 mL). The organic layer was separated and the aqueous layer was acidified to pH 4 using aq. citric acid solution (0.5 M). The precipitated solid was collected by filtration and then dried under reduced pressure to afford 2-amino-6-(benzyloxy) nicotinic acid as an off-white solid (220 g, yield=72%). $^1$H NMR (400 MHz, DMSO-d$_6$) δ=12.56-12.32 (m, 1H), 7.97-7.91 (m, 1H), 7.52-7.41 (m, 2H), 7.38-7.11 (m, 5H), 6.03 (d, J=8.5 Hz, 1H), 5.39-5.31 (m, 2H). LCMS Purity=93%; m/z=245.29 (M+H).

Step 2: Preparation of methyl 2-amino-6-(benzyloxy)nicotinate

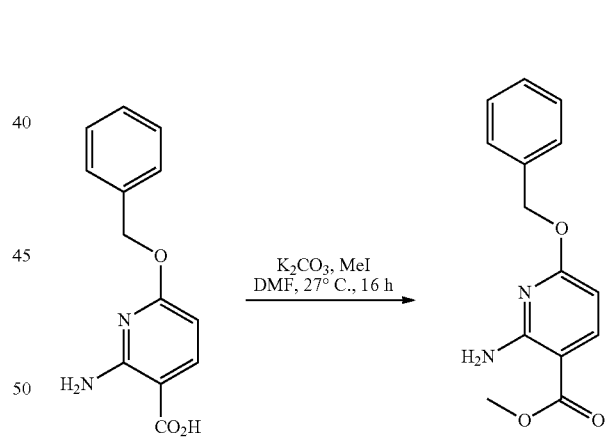

To a stirred solution of 2-amino-6-(benzyloxy)nicotinic acid (220 g, 901 mmol) in DMF (2.5 L) at 26° C. under N2 atmosphere were slowly added potassium carbonate (373 g, 2702 mmol) and iodomethane (0.282 L, 4504 mmol). The reaction mixture was stirred at 27° C. for 16 hr. The progress of reaction was monitored by TLC (SiO$_2$, 40% EtOAc/Pet., Rf=0.6). On completion, the reaction mixture was diluted with water (5 L). The precipitated solid was isolated by filtration and then dried under vacuum to afford methyl 2-amino-6-(benzyloxy)nicotinate as an off-white solid (220 g, yield=92%). $^1$H NMR (400 MHz, CDCl$_3$) δ=8.00 (d, J=8.4 Hz, 1H), 7.42-7.40 (m, 2H), 7.39-7.35 (m, 2H), 7.34-7.31 (m, 1H), 6.01 (d, J=8.4 Hz, 1H), 5.33 (s, 2H), 3.84 (s, 3H). LCMS Purity=97%, m/z=259.30 (M+H).

Step 1: Preparation of 2-amino-6-(benzyloxy) nicotinic acid

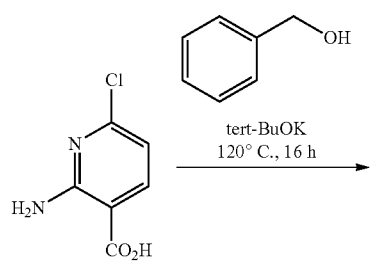

Step 3: Preparation of methyl 2-amino-6-hydroxynicotinate

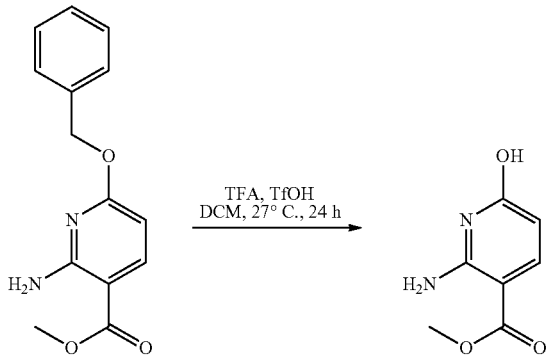 [SMILES: COC(=O)c1ccc(OCc2ccccc2)nc1N ; "TFA, TfOHDCM, 27° C., 24 h" ; COC(=O)c1ccc(O)nc1N]

To a stirred solution of methyl 2-amino-6-(benzyloxy)nicotinate (50 g, 190 mmol) in DCM (500 mL) at 26° C. under N2 atmosphere were slowly added TFA (800 mL) and triflic acid (25 mL, 282 mmol). The reaction mixture was stirred at 26° C. for 16 hr. The progress of reaction was monitored by TLC ($SiO_2$, EtOAc, Rf=0.2). On completion, the volatiles were removed under vacuum to afford the crude product. This material was triturated with diethyl ether (3×1000 mL) and the precipitated solid was then isolated by filtration. To the solid was added water (2 L) and the mixture was then 5 h. The solid was collected by filtration and was washed with water. The solid was dried under vacuum to afford methyl 2-amino-6-hydroxynicotinate as an off-white solid (25 g, yield=78%). 1H NMR (300 MHz, DMSO-d6) &=10.92-10.76 (m, 1H), 7.65 (d, J=9.5 Hz, 1H), 7.43-6.87 (m, 2H), 5.51 (d, J=9.5 Hz, 1H), 3.69 (s, 3H). LCMS Purity=99.32%; m/z=169.32 (M+H). The absence of TFA and triflic acid in the product was confirmed by $^{19}$F-NMR. The product was used directly in the next step without additional purification.

Step 4: Preparation of methyl 2-amino-6-(3,3,3-trifluoropropoxy)nicotinate

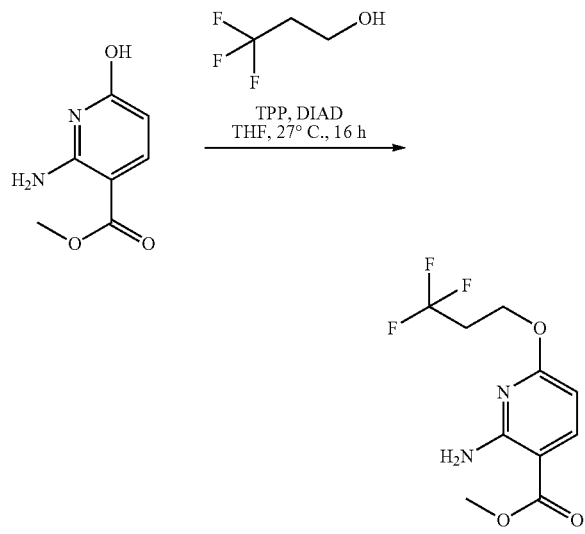

To a stirred solution of methyl 2-amino-6-hydroxynicotinate (50 g, 297 mmol) in THF (1000 mL) at 27° C. under nitrogen atmosphere was added triphenylphosphine (156 g, 595 mmol). The reaction mass was cooled to 0° C. and to the reaction mass was added drop-wise diisopropyl azodicarboxylate ("DIAD" 116 mL, 595 mmol). The solution was stirred for 30 min. To the solution at 0° C. was added a solution of 3,3,3-trifluoropropan-1-ol (52.4 mL, 595 mmol) in THF (200 mL). The reaction mass was then allowed to slowly warm to 27° C. and was then stirred at that temperature for 16 hrs. The progress of the reaction was monitored by TLC ($SiO_2$, 10% EtOAc/Pet. Rf=0.5). On completion, the reaction mixture was diluted with water (500 mL) and extracted with EtOAc (2×500 mL). The combined organics were washed with water (500 mL) and then brine solution (500 mL). The organic layer was dried over anhydrous $Na_2SO_4$, filtered, and then concentrated under reduced pressure to afford the crude product as a yellow semi-solid (100 g). This material was purified via silica gel chromatography eluting with 5-10% EtOAc in pet. The fractions containing the desired product were pooled and concentrated under reduced pressure to afford methyl 2-amino-6-(3,3,3-trifluoropropoxy)nicotinate as a as yellow liquid (50 g, 60% yield). $^1$H-NMR (400 MHz, $CDCl_3$) δ: 8.01 (d, J=8.8 Hz, 1H), 7.21-6.85 (brs, 1H), 6.04 (d, J=8.4 Hz, 1H), 4.50 (t, J=6.6 Hz, 2H), 3.84 (s, 3H), 2.63-2.55 (m, 2H). LCMS analysis method: Column=Acquity BEH C18 (50 mm×2.1 mm, 1.7 um); Mobile Phase A=0.05% Formic Acid in water; Mobile Phase B=0.05% Formic Acid in CAN; Gradient=Time (min.)/% B: 0/3, 0.4/3, 2.5/98, 3.4/98, 3.5/3, 4/3; Column Temp.=35° C.; Flow Rate=0.6 mL/min. LCMS result: retention time=2.03 mins.; observed ion=265.15 (M+H); LCMS Purity=93%.

Step 5: Preparation of 2-amino-6-(3,3,3-trifluoropropoxy)nicotinic acid

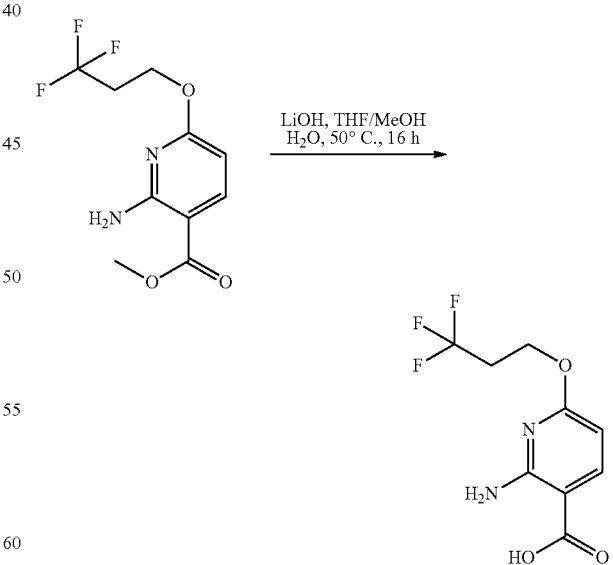

To a stirred solution of methyl 2-amino-6-(3,3,3-trifluoropropoxy)nicotinate (50 g, 189 mmol) in tetrahydrofuran (THF) (500 mL), methanol (150 mL) and water (80 mL) at 0° C. under nitrogen atmosphere was added lithium hydroxide monohydrate (22.66 g, 946 mmol). The reaction mixture was stirred at 50° C. for 16 hr. The progress of the reaction was monitored by TLC (SiO$_2$, 50% EtOAc/Pet. Rf=0.3). On completion, the reaction mixture was concentrated under reduced pressure to afford an aqueous residue. The residue was then acidified to pH 4 via the addition of 1N HCl. The resulting precipitate was collected via filtration and was washed with water (500 mL), then n-hexane (400 mL), and then dried to afford 2-amino-6-(3,3,3-trifluoropropoxy)nicotinic acid as an off-white solid (45 g, 90% yield). $^1$H-NMR (400 MHz, DMSO-d$_6$) δ: 12.47 (brs, 1H), 7.93 (d, J=8.8 Hz, 1H), 7.35 (brs, 2H), 5.98 (d, J=8.8 Hz, 1H), 4.44 (t, J=6.1 Hz, 2H), 2.84-2.73 (m, 2H). The product was used directly in the next step without further purification.

Alternate preparation of
2-amino-6-(3,3,3-trifluoropropoxy)nicotinic acid

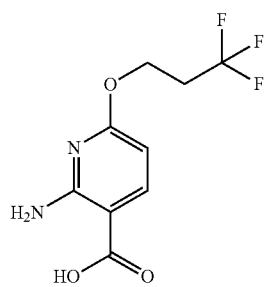 [SMILES: Nc1nc(OCCC(F)(F)F)ccc1C(=O)O]

Synthesis Scheme:

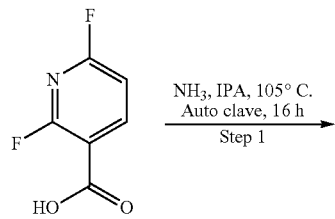

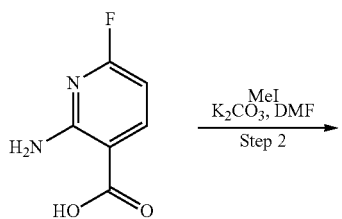

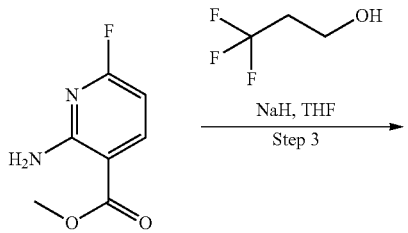

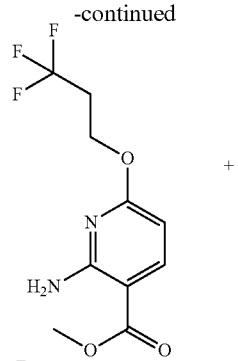

-continued

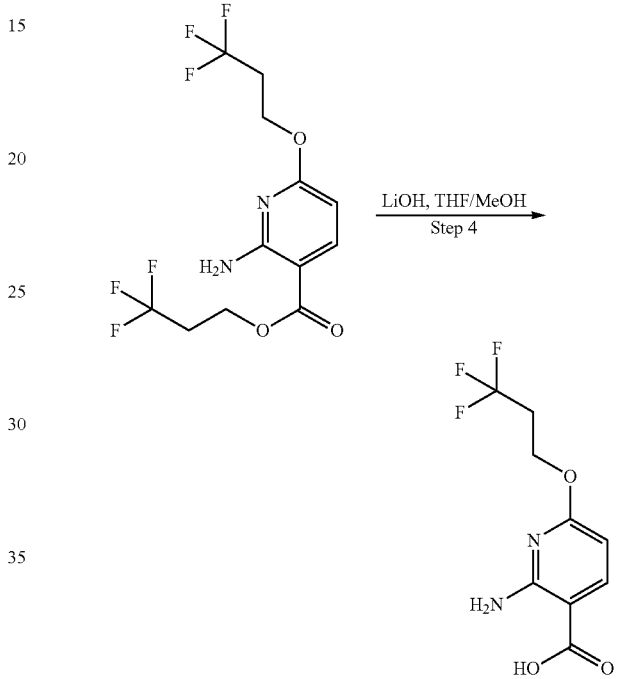

Step 1: Preparation of 2-amino-6-fluoronicotinic acid

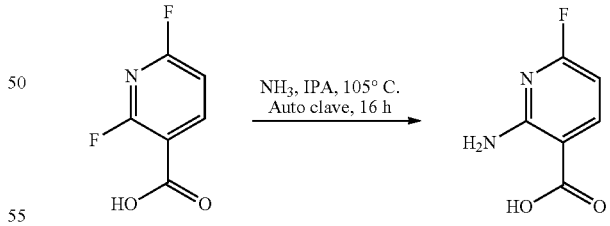

A mixture of NH$_3$ in water ("25% NH$_3$ in H$_2$O", 1 L, 4V) and isopropanol (6.5 L, 26V) at 0° C. was sparged ammonia gas for 1 hr. To the mixture in an autoclave (25 L) was added 2,6-difluoronicotinic acid (250 g, 1571 mmol). Then the reaction mixture was stirred at 105° C. for 20 hr. The progress of the reaction was monitored by TLC (SiO$_2$, 80% EtOAc/Pet. Rf=0.3). On completion, the reaction mixture was allowed to cool to 20° C. and then was concentrated under reduced pressure at below 20° C. to a volume of 4-6V (1.5 L). The residue was dissolved in water (5 L) and acidified to pH 2-3 via the addition of 2N HCl (700 mL) and then stirred for 2 hrs. The resulting precipitate was collected via filtration and was washed with water (4000 mL), then n-hexane (5000 mL), and then dried in a vacuum oven at 50° C. to afford 2-amino-6-fluoronicotinic acid as an off-white solid (250 g, 92% yield). This product was blended with the product of other batches prepared by the same method to afford 2000 g of combined product. Residual solvent was removed from the solids by suspending the solids in toluene (10 L) and then removing the toluene by distillation. The resulting solids were dried in a vacuum oven at 60° C. for 7 days to afford 2-amino-6-fluoronicotinic acid as an off-white solid (1.6 kg, 77% yield). $^1$H-NMR (400 MHz, DMSO-$d_6$) δ: 12.94 (brs, 1H), 8.17 (t, J=8.8 Hz, 1H), 7.56 (brs, 2H), 6.25 (dd, J=8.2, 2.8 Hz, 1H). LCMS Method: Column=Acquity BEH C18 (50 mm×2.1 mm, 1.7 um); Mobile Phase A=0.05% Formic Acid in water; Mobile Phase B=0.05% Formic Acid in acetonitrile; Gradient=Time (min)/% B: 0/3, 0.4/3, 2.5/98, 3.4/98, 3.5/3, 4/3; Column Temperature=35° C.; Flow Rate=0.6 mL/min. LCMS Result: retention time=1.24 mins.; observed ion=157.04 (M+H); LCMS Purity=96%.

Step 2: Preparation of methyl 2-amino-6-fluoronicotinate

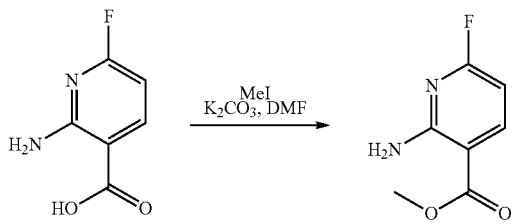

To a stirred solution of 2-amino-6-fluoronicotinic acid (150 g, 961 mmol) and potassium carbonate (398 g, 2882 mmol) in DMF (1500 mL) was added iodomethane (300 mL, 4804 mmol). The reaction mixture was stirred at 27° C. for 16 hr under nitrogen atmosphere. The progress of the reaction was monitored by TLC (SiO$_2$, 30% EtOAc/Pet. Rf=0.7). On completion, the reaction mixture was quenched by the addition of ice-cold water (5000 mL). The resulting precipitate was collected via filtration and was washed with water (2000 mL), then n-hexane (1000 mL), and then dried to afford methyl 2-amino-6-fluoronicotinate as a brown solid (120 g, 70% yield). $^1$H-NMR (400 MHz, DMSO-$d_6$) δ: 8.20 (t, J=8.8 Hz, 1H), 7.54 (brs, 2H), 6.29 (dd, J=8.4, 2.8 Hz, 1H), 3.82 (m, 3H). LCMS Method: Column=Acquity BEH C18 (50 mm×2.1 mm, 1.7 um); Mobile Phase A=0.05% Formic Acid in water; Mobile Phase B=0.05% Formic Acid in acetonitrile; Gradient=Time (min)/% B: 0/3, 0.4/3, 2.5/98, 3.4/98, 3.5/3, 4/3; Column Temp.=35° C.; Flow Rate=0.6 mL/min. LCMS Result: retention time=1.55 mins.; observed ion=171.07 (M+H); LCMS Purity=96%. The product was used directly in the next step without further purification.

Step 3: Preparation of methyl 2-amino-6-(3,3,3-trifluoropropoxy)nicotinate and 3,3,3-trifluoropropyl 2-amino-6-(3,3,3-trifluoropropoxy)nicotinate

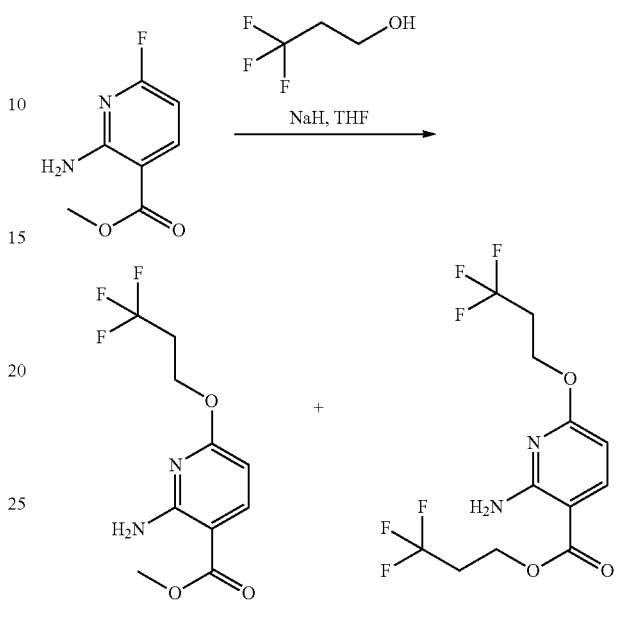

To a stirred solution of methyl 2-amino-6-fluoronicotinate (25 g, 147 mmol) and 3,3,3-trifluoropropan-1-ol (15.54 mL, 176 mmol) in THF (500 mL) at 0° C. under nitrogen atmosphere was added portion-wise sodium hydride (60% disp. in oil, 8.82 g, 220 mmol). The reaction mixture was stirred at 0° C. for 30 min and then allowed to slowly warm to 27° C. and stirred at that temperature for 16 hrs. The progress of the reaction was monitored by TLC (SiO$_2$, 10% EtOAc/Pet. Rf=0.5). On completion, the reaction mixture was cooled 0° C. and quenched with saturated aqueous NH$_4$Cl solution (300 mL). The mixture was extracted with EtOAc (2×500 mL). The combined organics were washed with brine solution (200 mL), dried over anhydrous Na$_2$SO$_4$, filtered, and then concentrated under reduced pressure to afford methyl 2-amino-6-(3,3,3-trifluoropropoxy)nicotinate as a yellow liquid (40 g). Formation of the transesterification byproduct 3,3,3-trifluoropropyl 2-amino-6-(3,3,3-trifluoropropoxy)nicotinate was also observed in the reaction. LCMS Method: Column=Acquity BEH C18 (50 mm×2.1 mm, 1.7 um); Mobile Phase A=0.05% Formic Acid in water; Mobile Phase B=0.05% Formic Acid in acetonitrile; Gradient=Time (min)/% B: 0/97, 0.4/97, 2.5/2, 3.4/2, 3.5/97, 4.0/97; Column Temp.=35° C.; Flow Rate=0.6 mL/min. LCMS Result: retention time=2.04 & 2.22 mins.; observed ion=265.18 & 347.29 (M+H); LCMS Purity=57% of methyl 2-amino-6-(3,3,3-trifluoropropoxy)nicotinate and 15% of 3,3,3-trifluoropropyl 2-amino-6-(3,3,3-trifluoropropoxy)nicotinate. This crude product mixture was blended with two other batches of crude products prepared by the same method (40 g and 50 g). The combined material (130 g) was purified by silica gel chromatography eluting with 10-20% EtOAc in pet. The fractions containing the desired product were pooled and concentrated under reduced pressure to afford a 6:1 mixture of methyl 2-amino-6-(3,3,3-trifluoropropoxy)nicotinate and 3,3,3-trifluoropropyl 2-amino-6-(3,3,3-trifluoropropoxy) nicotinate as a pale-yellow liquid (100 g, 90% yield). 1H-NMR (400 MHz, CDCl$_3$) δ: 8.02-7.97 (m, 1H), 7.04-

6.48 (m, 1H), 6.08-6.03 (m, 1H), 4.52-4.47 (m, 2H), 3.83 (s, 3H), 2.64-2.54 (m, 2H). LCMS Method: Column=Acquity BEH C18 (50 mm×2.1 mm, 1.7 um); Mobile Phase A=0.05% Formic Acid in water; Mobile Phase B=0.05% Formic Acid in acetonitrile; Gradient=Time (min)/% B: 0/97, 0.4/97, 2.5/2, 3.4/2, 3.5/97, 4.0/97; Column Temp.=35° C.; Flow Rate=0.6 mL/min. LCMS Result: retention time=2.02 & 2.21 mins.; observed ion=264.97 & 346.97 (M+H); LCMS Purity=66% of methyl 2-amino-6-(3,3,3-trifluoropropoxy)nicotinate and 11% of 3,3,3-trifluoropropyl 2-amino-6-(3,3,3-trifluoropropoxy)nicotinate.

Step 4: Preparation of
2-Amino-6-(3,3,3-trifluoropropoxy)nicotinic acid

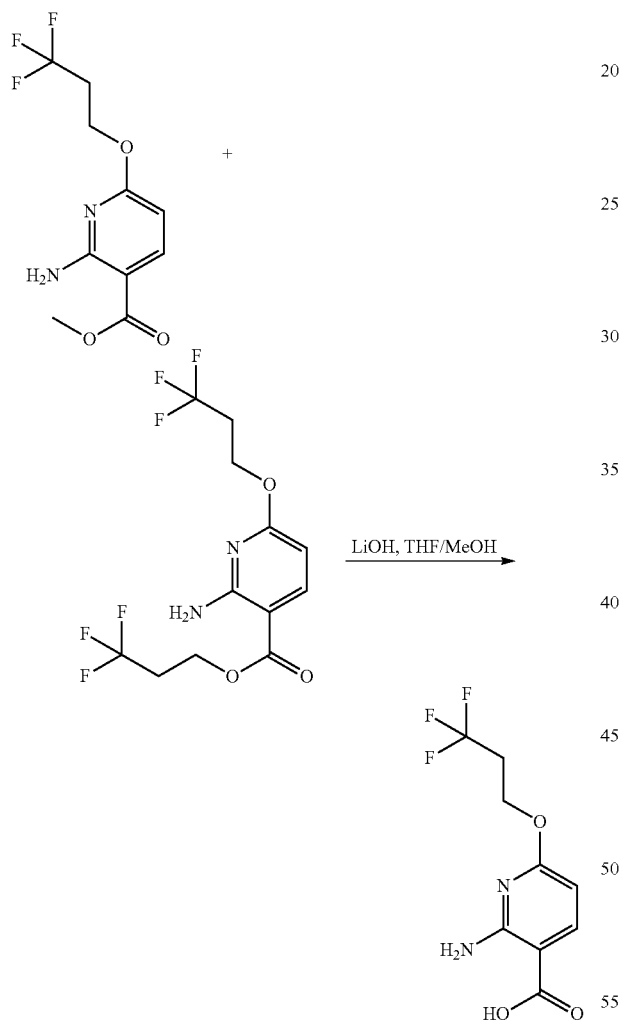

To a stirred solution of methyl 2-amino-6-(3,3,3-trifluoropropoxy)nicotinate and 3,3,3-trifluoropropyl 2-amino-6-(3,3,3-trifluoropropoxy)nicotinate (6:1, 100 g, 310 mmol) in tetrahydrofuran (THF) (800 mL), Methanol (300 mL) and water (200 mL) at 27° C. under nitrogen atmosphere was added lithium hydroxide monohydrate (37.2 g, 1552 mmol). The reaction mixture was stirred at 50° C. for 8 hr. The progress of the reaction was monitored by TLC (SiO$_2$, 50% EtOAc/Pet. Rf=0.3). On completion, the reaction mixture was concentrated under reduced pressure and the resulting aqueous residue was then acidified to pH 4 via the addition of 1N HCl. The resulting precipitate was collected via filtration and was washed with water (2000 mL), then n-hexane (1000 mL), and then dried to afford 2-amino-6-(3,3,3-trifluoropropoxy)nicotinic acid as an off-white solid (80 g, 97% yield). $^1$H-NMR (400 MHz, DMSO-d$_6$) δ: 12.47 (brs, 1H), 7.93 (d, J=8.4 Hz, 1H), 7.33 (brs, 2H), 5.99 (d, J=8.4 Hz, 1H), 4.45 (t, J=6.2 Hz, 2H), 2.83-2.74 (m, 2H). LCMS Method: Column=Acquity BEH C18 (50 mm×2.1 mm, 1.7 um); Mobile Phase A=0.05% Formic Acid in water; Mobile Phase B=0.05% Formic Acid in acetonitrile; Gradient=Time (min.)/% B: 0/3, 0.4/3, 2.5/98, 3.4/98, 3.5/3, 4/3; Column Temp.=35° C.; Flow Rate=0.6 mL/min. LCMS Result: retention time=1.73 mins.; observed ion=251.17 (M+H); LCMS Purity=94%. The product was used directly in the next step without further purification.

Alternate Preparation of Example 1: N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

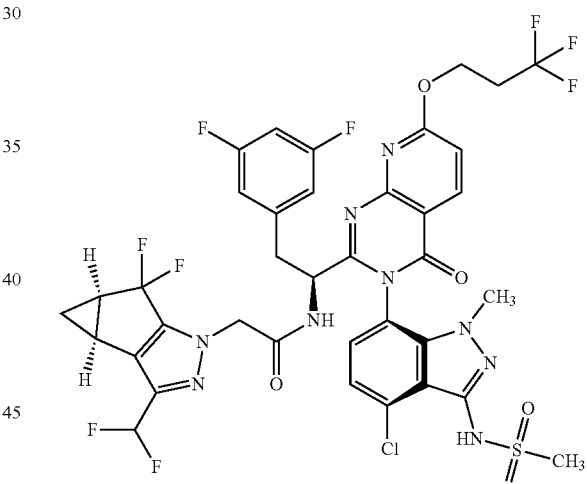

Synthesis Scheme:

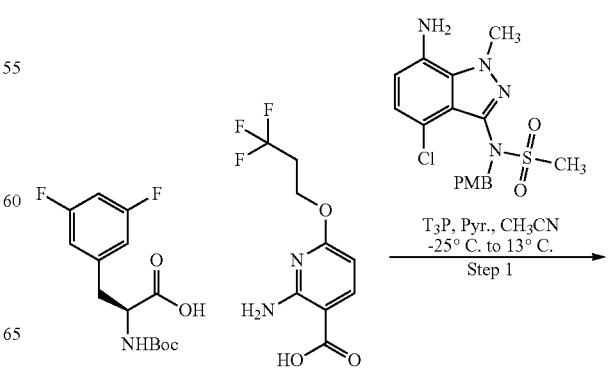

-continued

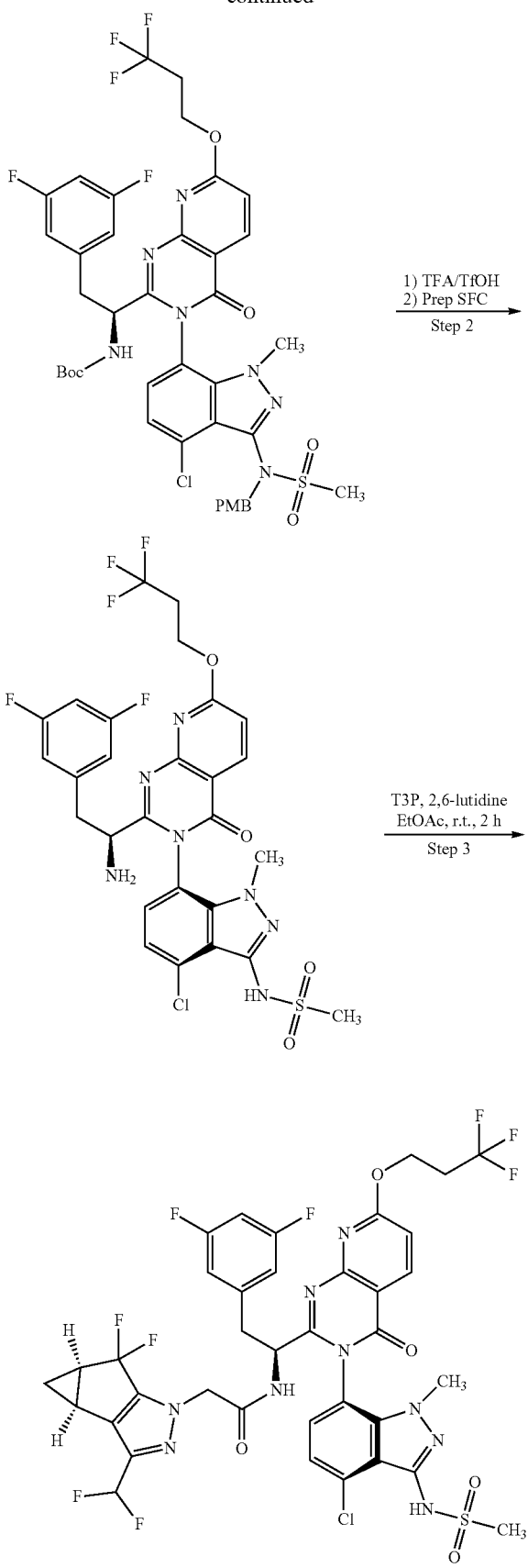

Step 1: Preparation of tert-Butyl (S)-(1-(3-(4-chloro-3-(N-(4-methoxybenzyl)methylsulfonamido)-1-methyl-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)carbamate

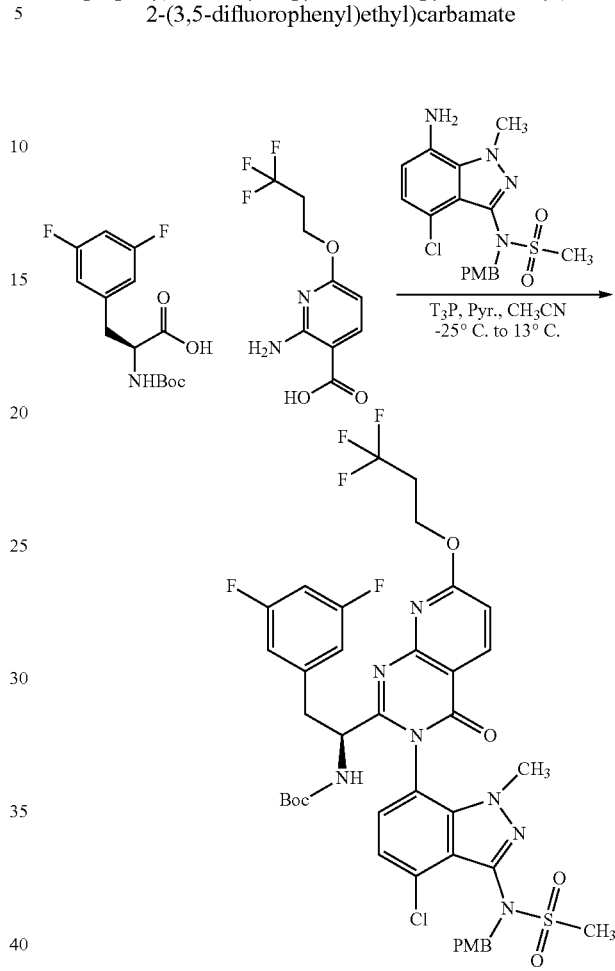

To a stirred solution of (S)-2-((tert-butoxycarbonyl)amino)-3-(3,5-difluorophenyl)propanoic acid (62.3 g, 207 mmol) and 2-amino-6-(3,3,3-trifluoropropoxy)nicotinic acid (55 g, 207 mmol) in acetonitrile (600 mL) under nitrogen atmosphere at −25° C. was added pyridine (41.8 mL, 517 mmol). To the resulting mixture was added drop-wise over 15 min. 2,4,6-tripropyl-1,3,5,2,4,6-trioxatriphosphinane 2,4,6-trioxide ("T3P", 50% wt in EtOAc, 609 mL, 1033 mmol). The solution was stirred at −25° C. for 1 hr, then was allowed to slowly warm to 13° C. and was stirred for 5 hrs. To the solution at 13° C. was added N-(7-amino-4-chloro-1-methyl-1H-indazol-3-yl)-N-(4-methoxybenzyl)methanesulfonamide (82 g, 207 mmol). The reaction mass was then allowed to slowly warm to 27° C. and was then stirred at that temperature for 16 hrs. The progress of the reaction was monitored by TLC (SiO2, 40% EtOAc/Pet. Rf=0.4). On completion, the reaction mixture was concentrated under reduced pressure. The residue was dissolved in EtOAc (500 mL) and then washed with aq. citric acid (0.5M, 2×500 mL) followed by aq. NaOH (1N, 3×500 mL). The organic layer was dried over Na2SO4, filtered and then concentrated under reduced pressure to afford the crude product (180 g) which was purified by silica gel chromatography eluting with 40-50% EtOAc in pet. The fractions containing the desired product were pooled and concentrated under reduced pressure to afford tert-butyl (S)-(1-(3-(4-chloro-3-(N-(4-methoxybenzyl)methylsulfonamido)-1-methyl-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)carbamate as an off-white solid (85 g, 39% yield). The product is a mixture of homochiral atropisomers (diastereomers). LCMS Method: Column=Acquity BEH C18 (50 mm×2.1 mm, 1.7 um); Mobile Phase A=0.05% Formic Acid in Water; Mobile Phase B=0.05% Formic Acid in acetonitrile; Gradient=Time (min)/% B: 0/3, 0.4/3, 2.5/98, 3.4/98, 3.5/3, 4/3; Column Temp.=35° C.; Flow Rate=0.6 mL/min. LCMS Result: retention time=2.46 mins.; observed ion=892.53 (M+H); LCMS Purity=85%.

Step 2: Preparation of (S)—N-((6P)-7-((3P)-2-(1-amino-2-(3,5-difluorophenyl)ethyl)-4-oxo-7-(3,3,3-trifluoropropoxy)pyrido[2,3-d]pyrimidin-3(4H)-yl)-4-chloro-1-methyl-1H-indazol-3-yl)methanesulfonamide

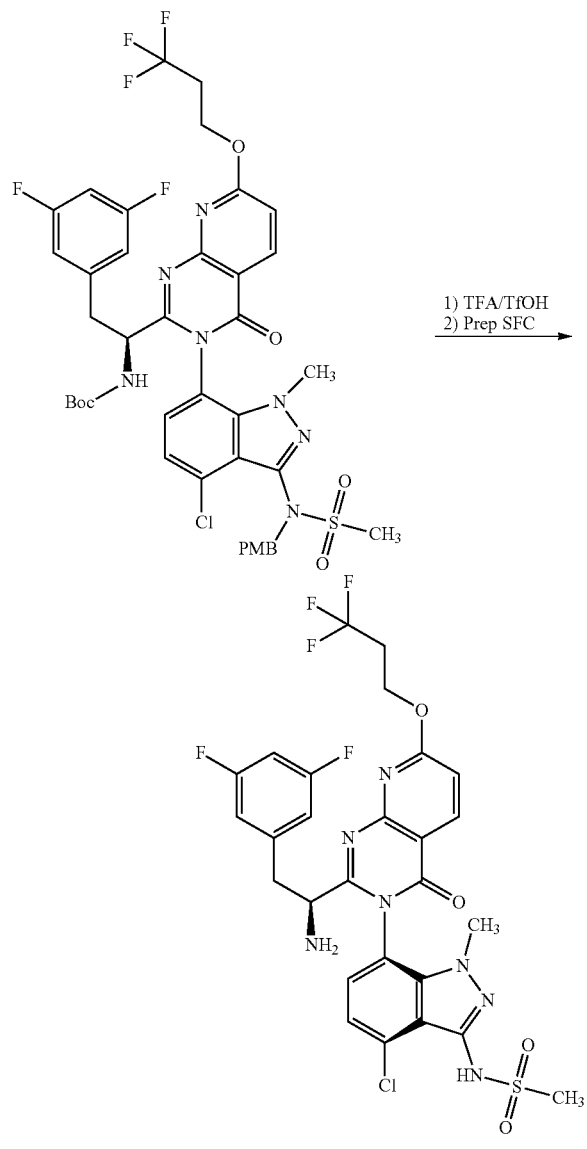

To a stirred solution of tert-butyl (S)-(1-(3-(4-chloro-3-(N-(4-methoxybenzyl)methylsulfonamido)-1-methyl-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)carbamate (85 g, 95 mmol) in DCM (300 mL) at 0° C. was added trifluoroacetic acid (TFA, 294 mL, 3810 mmol) followed by triflic acid (25.4 mL, 286 mmol). The solution was allowed to warm to 27° C. and stirred for 1 hr under nitrogen atmosphere. The progress of the reaction was monitored by TLC (SiO$_2$, 80% EtOAc/Pet. Rf=0.3). On completion, the volatiles were removed under a gentle stream of nitrogen gas. The residue was dissolved in EtOAc (1000 mL) and washed with 2N NaOH (2×500 mL) and then brine (500 mL). The organic layer was dried over Na$_2$SO$_4$, filtered, and then concentrated under reduced pressure to afford the crude product which was purified by silica gel chromatography eluting with 50-99% EtOAc in Pet. The fractions containing the desired product were pooled and concentrated under reduced pressure to afford (S)—N-(7-(2-(1-amino-2-(3,5-difluorophenyl)ethyl)-4-oxo-7-(3,3,3-trifluoropropoxy)pyrido[2,3-d]pyrimidin-3(4H)-yl)-4-chloro-1-methyl-1H-indazol-3-yl)methanesulfonamide as a pale yellow solid (63 g). The material is a mixture of homochiral atropisomers (diastereomers) in a 64:26 ratio as determined by LCMS. This product was blended with three additional batches of products prepared by following the same procedure. The combined product (195 g) was dissolved in methanol:acetonitrile (80:20, 1300 mL) and this solution was purified by prep-SFC using the following method: Column=(R,R) Whelk-01 (250×30×5p); eluent=CO$_2$:MeOH (65:35); Flow-rate=90 g/min; Back-pressure=120 bar; Detection=214 nm (UV); Stack time=14 min; Load per injection=430 mg. The pure major peak was collected and concentrated under reduced pressure to afford to afford the single stereoisomer (S)—N-((6P)-7-((3P)-2-(1-amino-2-(3,5-difluorophenyl)ethyl)-4-oxo-7-(3,3,3-trifluoropropoxy)pyrido[2,3-d]pyrimidin-3(4H)-yl)-4-chloro-1-methyl-1H-indazol-3-yl)methanesulfonamide as an off-white solid (113 g, 63% yield). $^1$HNMR (400 MHz, DMSO-d$_6$) δ: 8.42 (d, J=8.8 Hz, 1H), 7.43 (d, J=8.1 Hz, 1H), 7.37 (d, J=8.1 Hz, 1H), 7.06 (d, J=8.8 Hz, 1H) 7.03-6.97 (m, 1H), 6.75-6.70 (m, 2H), 4.73-4.69 (m, 2H), 3.68 (s, 3H), 3.58-3.52 (m, 1H), 3.28-3.24 (m, 1H), 3.22 (s, 3H), 2.97-2.83 (m, 3H). LCMS Method: Column=XBridge C18 (75 mm×4.6 mm, 3.5 μm); Mobile Phase A=5 mM ammonium bicarbonate in water; Mobile Phase B=acetonitrile; Gradient=Time (min)/% B: 0/5, 0.5/5, 1.0/15, 4.0/98, 7.0/98, 7.5/5, 8.0/5; Column Temp=35° C.; Flow Rate=1.3 mL/min. LCMS Result: retention time=4.03 mins.; observed ion=672.07 (M+H); LCMS Purity=98%; HPLC Purity=98%; Chiral HPLC Purity=98%.

Step 3: Preparation of N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

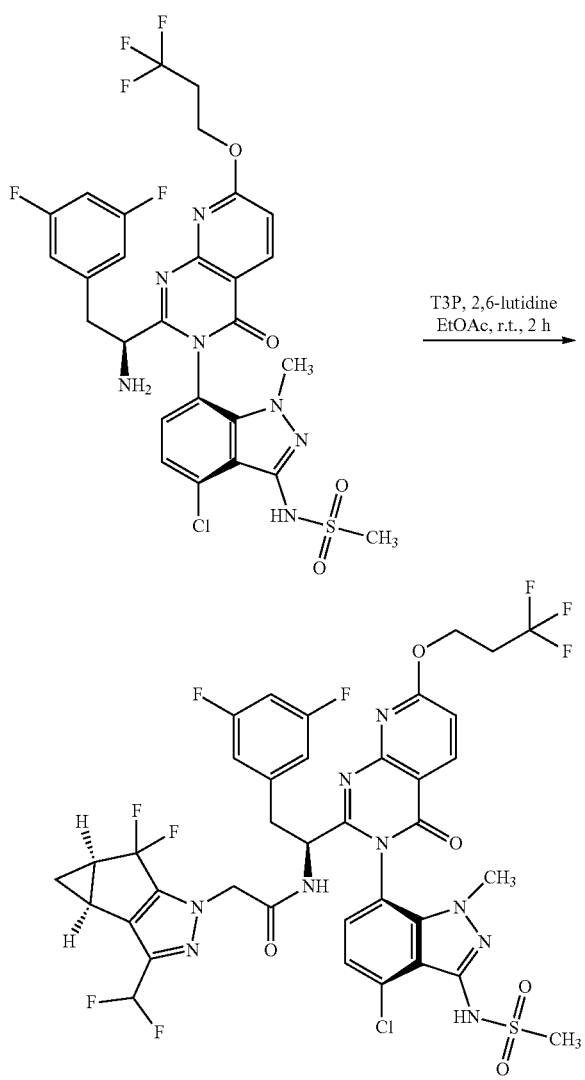

To a stirred solution of (S)—N-((6P)-7-((3P)-2-(1-amino-2-(3,5-difluorophenyl)ethyl)-4-oxo-7-(3,3,3-trifluoropropoxy)pyrido[2,3-d]pyrimidin-3(4H)-yl)-4-chloro-1-methyl-1H-indazol-3-yl)methanesulfonamide (55 g, 82 mmol) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (22.70 g, 86 mmol) in ethyl acetate (818 ml) was added 2,6-lutidine (23.83 ml, 205 mmol). To the mixture was added drop-wise 2,4,6-tripropyl-1,3,5,2,4,6-trioxatriphosphinane 2,4,6-trioxide ("T3P", 50% wt. in ethyl acetate) (97 mL, 164 mmol) upon which the internal temperature rose from 17° C. to 24° C. The mixture was stirred for 2 hrs at room temperature. The reaction was quenched by the addition of water (500 mL). The phases were partitioned and the organic phase was washed with water (500 mL), then dried over $Na_2SO_4$. The mixture was filtered and the filtrate was concentrated to ¼ of the original volume to afford the crude product as a solution in ethyl acetate.

A second batch of product was prepared following the same procedure modified as follows: the reaction was conducted using (S)—N-((6P)-7-((3P)-2-(1-amino-2-(3,5-difluorophenyl)ethyl)-4-oxo-7-(3,3,3-trifluoropropoxy)pyrido[2,3-d]pyrimidin-3(4H)-yl)-4-chloro-1-methyl-1H-indazol-3-yl)methanesulfonamide (53.4 g, 79 mmol) and the amounts of all other reagents were adjusted accordingly. The workup concluded with a brine (300 mL) wash before drying over $MgSO_4$.

The crude products were combined and then adsorbed onto Celite. The resulting powder was subjected to silica gel chromatography (3 kg RediSep Gold column) eluting with 30-85% ethyl acetate in hexanes. Fractions containing the desired product were pooled and concentrated under reduced pressure to afford a yellow foam. The material was placed under high vacuum for 18 h. The material was converted to a fine powder using a mortar and pestle and the solids were placed in vacuum oven at 50° C. for 48 h to afford N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as a yellow powder (134.1 g, 90% yield). $^1$H NMR (500 MHz, DMSO-$d_6$) δ ppm 9.84-9.91 (1H, m) 9.49 (1H, d, J=8.34 Hz) 8.47 (1H, d, J=8.35 Hz) 7.79 (1H, d, J=7.75 Hz) 7.49 (1H, d, J=8.05 Hz) 7.11 (1H, d, J=8.64 Hz) 6.80-7.09 (2H, m) 6.66 (2H, dd, J=8.20, 2.24 Hz) 4.69-4.75 (3H, m) 4.57 (1H, d, J=16.39 Hz) 4.48 (1H, ddd, J=11.03, 8.35, 2.68 Hz) 3.51 (3H, s) 3.42 (1H, dd, J=14.01, 2.38 Hz) 3.20 (3H, s) 3.05 (1H, dd, J=14.01, 11.03 Hz) 2.89-2.99 (2H, m) 2.42-2.48 (2H, m) 1.32-1.40 (1H, m) 0.81-0.86 (1H, m). LCMS Method: Column=Acquity UPLC BEH C18 (2.1×100 mm, 1.7 um particles); Solvent A=Water:MeCN (95:5) with 0.1% v/v Formic Acid; Solvent B=MeCN:Water (95:5) with 0.1% v/v Formic Acid; Gradient=Time (min)/% B: 0/0, 3.5/100, 4.5/100; Flow rate=0.8 mL/min. LCMS Result: retention time=3.173 min; observed mass=917.95 (M+H). UPLC purity=99.8%.

Naming of Example 1

The compound of Example 1 as prepared above is a homochiral material that contains axial chirality. Axial chirality can be described using P/M nomenclature as detailed in the IUPAC Gold Book (doi:10.1351/goldbook.A00547). However, at this time only a limited number of software tools are available which are capable of generating chemical names containing P/M nomenclature, and even fewer options are available to convert chemicals names using this nomenclature to structural representations of the molecules. Therefore, for clarity and convenience several names for Example 1 are provided below:

The name of Example 1 as generated by ChemDraw Ultra 12 (absent P/M nomenclature) is:

N—((S)-1-(3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide The chemical name of Example 1 as generated by JChem for Excel (including P/M nomenclature) is:

N-[(1S)-1-[(3P,3P)-3-(4-chloro-3-methanesulfonamido-1-methyl-1H-indazol-7-yl)-4-oxo-7-(3,3,3-trifluoropropoxy)-3H,4H-pyrido[2,3-d]pyrimidin-2-yl]-2-(3,5-difluorophenyl)ethyl]-2[(2S,4R)-9-(difluoromethyl)-5,5-difluoro-7,8-diazatricyclo[4.3.0.0$^{2,4}$]nona-1(6),8-dien-7-yl]acetamide The chemical name generated by ChemDraw Ultra 12 with manually added P/M nomenclature is:

N—((S)-1-((3P)-3-(4-chloro-1-methyl-3-(methylsulfonamido)-1H-indazol-7-yl)-4-oxo-7-(3,3,3-trifluoropropoxy)-3,4-dihydropyrido[2,3-d]pyrimidin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide Comparative Tests:

The compound of Example 1 was compared to the compound of Example 60.2 described in WO2018203235 (Scheme 1) in a number of tests. For the purposes of these comparisons we elected to use homochiral material of each compound as this level of purity is most representative of what would be used in human clinical trials. Specifically, restricted rotation about the indicated C—N bond of the indazole gives rise to atropisomers (diastereomers) in both Example 1 and Example 60.2 which can be separated by chromatography and are non-interconverting at room temperature. Thus, using chromatography we isolated in pure form the stereoisomers depicted in Scheme 2.

Scheme 1

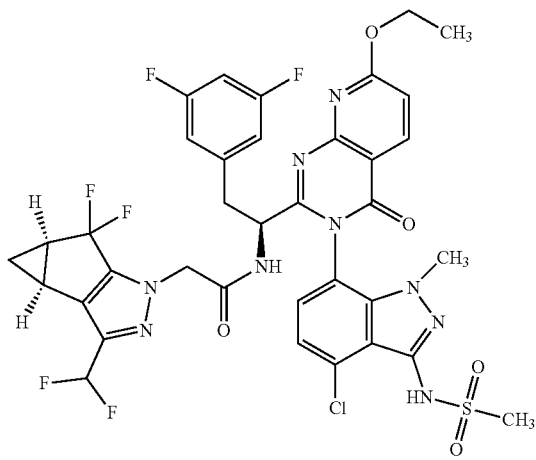

Example 60.2 as depicted in WO2018203235

Scheme 2

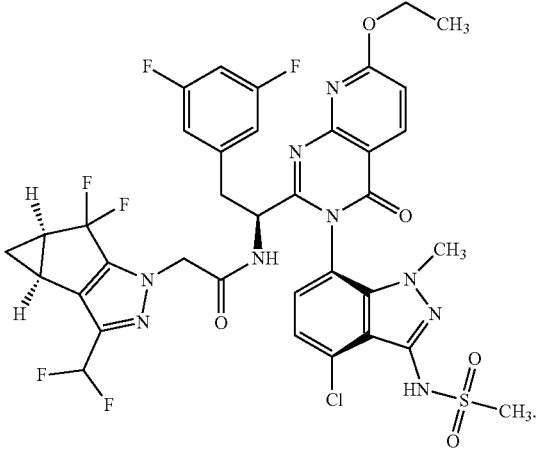

Example 60.2 depicting the stereochemistry of the homochiral material used in the described comparative tests.

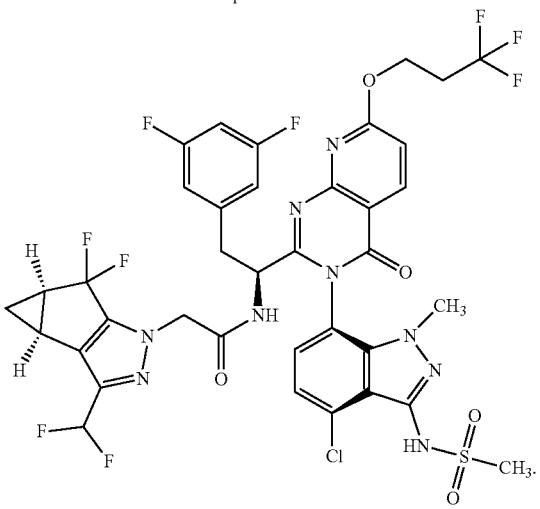

Example 1 of the present patent depicting the stereochemistry of the homochiral material used in the described comparative tests.

General procedure for quantifying compound via LC-MS/MS:

All in vitro samples were injected on an Exion LC 4500 Triple Quad™ LC-MS/MS system. The analytical column used was a Phenomenex C18 (C18, 4.6 mm×50 mm, 5 μm) maintained at room temperature. Mobile Phase A consisted of 0.1% (v/v) formic acid in MilliQ water. Mobile Phase B consisted of 100% methanol. The flow rate was 1 mL/min. The gradient was as follows: Mobile B was linearly increased from 5% to 90% over 0.7 min, maintained at 90% for 1.4 min, and maintained at 5% for 0.7 min.

All in vivo samples were injected on a Triple Quad™ 6500 LC-MS/MS system with columns maintained at 60° C. Mobile Phase A consisted of $H_2O$, 1 mM $NH_4OAc$, 0.025% Formic Acid. Mobile Phase B consisted of MeOH, 5 mM $NH_4OAc$. The flow rate was 0.6 mL/min. The column and elution gradient was selected from one of the general analysis methods described below.

General Analysis Method A:
Column=Waters X-Bridge BEH C18 (2.1×50 mm, 1.7 µm particles); Gradient: Time(min.)/% B=0.0/10, 0.2/10, 0.8/90, 1.3/90, 1.31/10, 2.0/10.

General Analysis Method B:
Column=Waters BEH C18 (2.1×50 mm, 2.5 µm particles); Gradient: Time(min.)/% B=0.0/10, 0.2/10, 0.8/90, 1.3/90, 1.31/10, 2.0/10.

General Analysis Method C:
Column=Waters BEH C18 (2.1×50 mm, 1.7 µm particles); Gradient: Time(min.)/% B=0.0/2, 0.40/2, 0.7/65, 1.3/90, 1.9/90, 1.91/2, 2.5/2.

Procedure to Measure Potency and Cytotoxicity:

MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 mg/ml penicillin G and up to 100 units/mL streptomycin. The 293T cells were propagated in DMEM media supplemented with 10% heat inactivated FBS, 100 mg/mL penicillin G and 100 mg/mL streptomycin. A recombinant $NL_{4-3}$ proviral clone, in which a section of the nef gene was replaced with the *Renilla* luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, WI). Supernatant was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, WI). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where $(Fa)=1/[1+(ED_{50}/drug\ conc.)m]$ (Johnson V A, Byington R T. Infectivity Assay. In Techniques in HIV Research. ed. Aldovini A, Walker BD. 71-76. New York: Stockton Press. 1990). The 50% inhibitory concentration ($EC_{50}$) was calculated by using the exponential form of the median effect equation where percent inhibition=$1/[1+(EC_{50}/drug\ concentration)m]$, where m is a parameter that reflects the slope of the concentration-response curve.

Compound cytotoxicity and the corresponding $CC_{50}$ values were determined using the same protocol as described in the antiviral assay except that uninfected cells were used. Cytotoxicity was assessed on day 4 in uninfected MT2 cells by using an XTT (2,3-bis[2-Methoxy-4-nitro-5-sulfophenyl]-2H-tetrazolium-5-carboxyanilide inner salt)-based colorimetric assay (Sigma-Aldrich, St Louis, Mo).

Results:

The potencies of Example 1 and Example 60.2 are within the error of the initial anti-HIV virology assay ($EC_{50}$ Example 1=25±8 µM, $EC_{50}$ Example 60.2=18±13 µM). Note that the $EC_{50}$ of Example 1 was 0.034 nM when initially tested, however, further tested resulted in a revised average of 25±8 µM. The cytotoxicity $CC_{50}$ measured is >0.5 µM and >10 µM for Example 1 and Example 60.2, respectively.

Procedure to Measure Metabolism in Liver Microsomes:

Liver microsomes from human, rat dog and monkey were thawed and diluted to a final concentration of 1 mg/mL in 100 mM potassium phosphate buffer (pH 7.4). Test compounds and controls were prepared at 100× final concentration of 1 µM in 1:1 acetonitrile:water (v/v) and aliquoted into microsomal mixture. The mixture was preincubated at 37° C. in a shaking water bath for 10 minutes. The incubations were performed in duplicate. Three controls were included in the incubations; warfarin, phenacetin, and verapamil. After the preincubation, the reaction was initiated with NADPH at a final concentration of 1 mM. At 0, 5, 15, 30, 45 and 60 minutes, 25 µL of sample was removed and quenched with 300 µL of acetonitrile containing internal standard (Telmisartan). The samples were vortexed for 5 minutes at 1200 rpm and then centrifuged at 4000 rpm for 10 min. A 100 µL aliquot of supernatant was diluted three-fold with water and injected on an Exion LC 4500 Triple Quad LC-MS/MS system. Results were reported as a percentage of parent remaining and was calculated from peak area ratios of test compound remaining after at each time point and compared to time zero incubation.

Results:

Example 1 is six times more stable in dog liver microsomes than Example 60.2, and Example 1 is at least two times more stable in monkey liver microsomes than Example 60.2. This data suggest that Example 1 should be significantly more stable than Example 60.2 to metabolism in vivo in dog and monkey.

TABLE 1

| Liver microsome stability | Example 1 | Example 60.2 |
|---|---|---|
| Human liver microsome $T_{1/2}$ | >120 min. | >120 min. |
| Rat liver microsome $T_{1/2}$ | >120 min. | >120 min. |
| Dog liver microsome $T_{1/2}$ | 105 min. | 17 min. |
| Monkey liver microsome $T_{1/2}$ | >120 min. | 55 min. |

Procedure to Measure Metabolism in Human Hepatocytes:

Cryopreserved hepatocytes in suspension from human, monkey, dog, rat and mouse were thawed and diluted in pre-warmed William's Medium E (pH 7.4). Aliquots of the hepatocyte suspension were added to test compound working solutions prepared in pre-warmed William's Medium E (pH 7.4) to achieve final concentrations of 0.5 µM in $0.5×10^6$ cells per milliliter and ≤0.25% DMSO. These samples were incubated at 37° C. with 5% carbon dioxide and shaking at 200 rpm. The incubations were performed in singlet. At time points 0, 10, 30, 60, 120 and 240 minutes, a 50 µL aliquot of the incubation mixtures was removed and added to a 100 µL solution of acetonitrile containing internal standard and the mixture was vortexed and then centrifuged at 4° C. and 3500 rpm for 15 minutes. Following completion of the experiment, samples were analyzed by LC-MS/MS. Metabolic stability results were reported as a percentage of parent test compound remaining. This percentage is calculated by dividing the peak area ratio of test compound following incubation ($t_x$) by the peak area ratio of test compound at time-zero ($t_0$) just prior to incubation.

The elimination rate constant (k, $min^{-1}$) is calculated using nonlinear regression fitting with the following equation:

$$C_t = C_0 \times e^{(-k \times t)}$$

where:
$C_0$ is the initial concentration represented as the peak area ratio (test compound peak area/internal standard peak area);
$C_t$ is the concentration at t represented as the area ratio (test compound peak area/internal standard peak area);
e is the base of the natural logarithm
t is the time (min);
k is the elimination rate constant ($min^{-1}$).

The half-life ($t_{1/2}$, min) is calculated using the following equation:

$$t_{1/2} = \frac{0.693}{k}$$

where:
k is the elimination rate constant (min$^{-1}$).
The in vitro intrinsic clearance ($CL_{int}$, mL/min/million cells) is calculated using the following equation:

$CL_{int} = 0.693/t_{1/2}/n$ where:
$t_{1/2}$ is the half-life;
n is the number of cells per mL.

Results:

The half-life of Example 1 in human hepatocytes was calculated to be >480 minutes while the half-life of Example 60.2 in human hepatocytes was calculated to be 350 minutes. The intrinsic clearance of Example 60.2 in human hepatocytes is 0.465 mL/min/g liver which is 1.5 times more rapid than the 0.312 mL/min/g liver clearance found with Example 1.

Procedure for Measuring Pharmacokinetic Parameters (PK) In Vivo:

PK was investigated in male CD1 mice, Wistar Han Rats, Cynomolgus monkeys, and Beagle Dogs. Two groups of animals (N=3 per group) received test compound either as an intravenous (IV) dose (1 mg/kg) or by oral gavage (5 mg/kg solution and suspension). Drug was formulated in 90% PEG 400, 10% ethanol for IV administration and in 90% PEG400, 5% ethanol for PO administration. Blood samples were collected at 0.167, 0.25, 0.5, 0.75, 1, 2, 3, 5, 7, 24, 48, 72 and 96 h post dose for IV; 0.25, 0.5, 0.75, 1, 2, 3, 5, 7, 24, 48, 72 and 96 h post dose for oral. Blood samples were collected into K$_3$EDTA tubes and centrifuged at 1500 to 2000×g to obtain plasma. Plasma samples were stored at −20° C. until analysis by LC-MS/MS. All in vivo samples were injected on an Exion LC 4500 Triple Quad™ LC-MS/MS system where the column was maintained at 60° C. and the flow rate was 0.6 mL/min. All LC-MS/MS analysis parameters are captured electronically in the raw data files. Rat IV, Dog IV, Monkey IV, and Monkey PO PK samples were analyzed by General Analysis Method A. Mouse IV, Mouse PO, and Dog PO PK samples were analyzed by General Analysis Method B. Rat PO samples were analyzed by General Analysis Method C.

The PK parameters were obtained by non-compartmental analysis of plasma concentration vs time data (Phoenix WinNonlin v8.1). The peak concentration ($C_{max}$) and time for $C_{max}$ ($T_{max}$) were recorded directly from experimental observations. The area under the curve from time zero to the last sampling time [AUC$_{0-T}$] and the area under the curve from time zero to infinity [AUC$_{INF}$] were calculated using the linear-log trapezoidal rule. The total plasma clearance ($CL_{Tp}$), steady-state volume of distribution ($V_{SS}$), apparent elimination half-life (T-HALF), and mean residence time (MRT) were estimated after IV administration. Estimations of AUC and T-HALF were made using a minimum of three timepoints with quantifiable concentrations. The absolute oral bioavailability (F) was estimated as the ratio of dose-normalized AUC values following oral and IV doses.

Results:

The IV pharmacokinetic (PK) parameters of Example 1 and Example 60.2 were measured in four pre-clinical species: mouse, rat, dog and monkey. Example 1 exhibited improved clearance in all four species relative to Example 60.2. Consistent with the results of liver microsome assay mentioned above, the differences in clearance was most significant for dog and monkey where clearance was improved 4.9-fold and 2.6-fold, respectively. Likewise, the half-life of Example 1 in circulation in dog and monkey was 3.4-fold and two-fold higher than Example 60.2, respectively.

TABLE 2

| Example 1 PK Parameters | Unit | Mouse | Rat | Monkey | Dog |
|---|---|---|---|---|---|
| CL | mL/min/kg | 0.50 | 2.64 | 8.50 | 1.68 |
| Vss | L/kg | 0.24 | 3.34 | 1.18 | 0.83 |
| $T_{1/2}$ | h | 7.6 | 17.4 | 3.0 | 8.6 |

TABLE 3

| Example 60.2 PK Parameters | Unit | Mouse | Rat | Monkey | Dog |
|---|---|---|---|---|---|
| CL | mL/min/kg | 5.20 | 5.89 | 22.2 | 8.21 |
| Vss | L/kg | 2.14 | 2.86 | 1.34 | 0.96 |
| $T_{1/2}$ | h | 5.2 | 11.0 | 1.4 | 2.5 |

Before a prospective medicine can enter human clinical trials, the safety of the compound typically should be assessed in two pre-clinical species: one rodent and one non-rodent. These species are commonly rat, and either dog or monkey. One objective of an in vivo safety study is to achieve concentrations of drug in circulation that are many times higher than what would be expected if a human were given an efficacious dose of the drug. The fold-difference between the drug concentrations achieved in the safety study versus the drug concentrations that would be expected in a person taking an efficacious dose of the drug is termed the "margin". Achieving high margins in a safety study is important because as margins increase so does the confidence that if a drug-related adverse event were possible it would be observed during the pre-clinical safety assessment.

Improved PK parameters in rat, dog or monkey mean that a lower dose of compound would be required to achieve a high concentration of drug in circulation for these pre-clinical species. Therefore, a monkey or dog given a dose of Example 1 would achieve higher margins than if given the same size dose of Example 60.2. Due to practical limitations of dose size, the margin (and therefore the confidence) that could be achieved with Example 1 in a non-rodent safety assessment study is higher than the margin that could be achieved with Example 60.2.

Procedure for allometric scaling of pre-clinical PK parameters to provide a prediction of dose in human:

Human dose predictions were performed using Phoenix WinNonlin (v 8.0) software and Microsoft Excel using the ModelRisk add-in for population modeling. Human estimates for each compound's $CL_{Tp}$ were obtained based on average allometric scaling of mouse, rat, monkey and dog IV data (body weight scaling factor of 0.75) and an average (body weight scaling factor of 1.0) from all species for $V_{SS}$. Human IV parameters (Vc, Ka, K12, K21, Kel) were determined using Mean Residence Time (MRT) scaling from preclinical species (mouse, rat, dog and cyno) using the human $V_{SS}$ and $CL_{Tp}$ estimates. Absorption (Ka) was determined by deconvolution (PO) or from the half-life (SC) in preclinical species (Ka=LN(2)/t1/2). The predicted human dose for PO and SC is calculated with consideration of human variability and is calculated to cover 95% of the human population.
Results:

Pre-clinical species PK parameters are commonly used to predict human PK parameters prior to human-clinical trials. The methods used for this predication are called "allometric scaling" and are generally discussed and practiced in the literature. Using allometric scaling, the predicted once-daily oral dose required to maintain an efficacious plasma concentration of drug in human is 7-fold lower for Example 1 than for Example 60.2. Specifically, the predicted human QD PO dose of Example 1 is less than 10 mg while the predicted human QD PO dose of Example 60.2 is greater than 30 mg.

While idiosyncratic drug reactions (i.e., hypersensitivity reactions) are unpredictable and serious in nature, and thus represent a significant clinical problem, it has been stated that drugs given at a daily dose of 10 mg or less are rarely if ever associated with a high incidence of idiosyncratic drug reactions (Uetrecht, J. P. New Concepts in Immunology Relevant to Idiosyncratic Drug Reactions: The "Danger Hypothesis" and Innate Immune System. Chem. Res. Toxicol. 1999, 12(5), 387-395, DOI:10.1021/tx980249i).

Procedure for Measuring Pharmacokinetic Parameters in a Subcutaneous In Vivo Experiment:

Drug was formulated in 1% Kolliphor P188/1% PEG3350/3.5% Mannitol/94.5% Water and then administered to Wistar Han Rats as a subcutaneous injection at a dose of 20 mg/kg. Blood samples were collected at 0.167, 0.25, 0.5, 0.75, 1, 2, 3, 5, 7, 24, 48, 72, 96 h, and then every 3 days for up to 122 days. Blood samples were collected into $K_3EDTA$ tubes and centrifuged at 1500 to 2000×g to obtain plasma. Plasma samples were stored at −20° C. until analysis by LC-MS/MS.
Results:

The suitability of each compound for subcutaneous (SC) administration was evaluated in a rat SC PK experiment. As determined by this experiment, the apparent half-life of compound in plasma was 13 days for Example 1 and 11.5 days for Example 60.2. The $AUC_{0-infinity}$ for Example 1 was 4,941 days*ng/mL (2.89% of the AUC extrapolated). The $AUC_{0-infinity}$ for Example 60.2 was 609 days*ng/mL (12.8% of the AUC extrapolated). The bioavailability was 93% for Example 1 and 25% for Example 60.2. Drug concentrations were maintained above 7 ng/mL for all animals for 73 days with Example 1, and 24 days with Example 60.2 (FIG. 1). Predicted once-monthly subcutaneous (Q1M SC) doses for human were calculated using the apparent half-lives and bioavailability derived from SC rat PK in conjunction with the predicted human clearance values derived from allometric scaling. The predicted Q1M SC dose required to maintain an efficacious plasma concentration of drug in human is 15-fold lower for Example 1 than for Example 60.2.

Procedure for Measuring Cytochrome P450 Induction in Cryopreserved Human Hepatocytes:

Following the guidance of the FDA ("In Vitro Metabolism- and Transporter-Mediated Drug-Drug Interaction Studies Guidance for Industry"), the potential of Example 1 and Example 60.2 to induce CYP2B6 expression was tested using hepatocytes from the same three individual donors (rather than pooled donors), and changes in enzyme mRNA levels were evaluated using the "fold-change method". In this test a fold-change in mRNA levels less than 2-fold is considered a negative finding, while a change 2-fold is considered a positive finding.

Compounds were tested in a CYP induction assay using inducible cryopreserved human primary hepatocytes from three donors to determine the potential to cause induction (as measured by an increase in mRNA transcription) of CYP2B6. Test compounds (0.12 to 30 μM final concentration) were incubated for 48 hours with primary human hepatocytes naturally expressing all nuclear receptors involved in regulation of expression levels of various CYP enzymes. Fresh solutions of test compounds and controls were diluted in assay media and added every 24 hours for two consecutive days, with a final DMSO concentration of 0.1%. At the end of the incubation, the integrity of cell monolayers, cell density and viability were evaluated to assess cytotoxicity effects. The cells were then solubilized in cell lysis buffer and total RNA was purified from each assay sample. Samples were then used in reverse transcription polymerase chain reactions (RT-PCR) to quantify the amount of specific mRNA species encoding the human CYP2B6 gene.

The induction potential of test compounds and controls was compared to known CYP2B6 inducer Phenobarbital (1000 μM). The results of this assay are expressed as fold induction. Fold induction was calculated as a ratio of mRNA level in cells treated with test compound over that in cells treated with DMSO (solvent control) alone, the basal mRNA level, and thus represents the induction potential of the test compound. Fold induction values were used to calculate percent of control activity values, which were then fitted to a 4-parameter logistic regression model to determine the $EC_{50}$ and $E_{max}$ values (if there is induction observed). The cytotoxicity was also assessed in parallel to avoid false positive CYP induction results due to cytotoxicity. Assessment and interpretation of CYP induction potential at cytotoxic concentrations should be avoided.
Results:

No cytotoxicity was observed with either compound at any of the concentrations tested (up to 30 μM). For Example 1, a negative finding (no induction) was found with all three donors. For Example 60.2, a positive finding (induction) was found with 2 of 3 donors ($EC_{50}$ values of 1.5 μM and 1.8 μM).

Induction of CYP enzyme expression is recognized as a root cause of drug-drug interactions, leading to increased clearance of the victim drug whose metabolism is governed by the induced CYP isoform. Among the CYP isoforms, CYP2B6 is of particular importance in the context of HIV treatment because efavirenz (EFV), a medicine widely used to treat HIV (included on the 2019 World Health Organization list of essential medicines), is primarily metabolized by CYP2B6 (Ward, B. A., Gorski, J. C., Jones, D. R., Hall, S. D., Flockhard, D. A., Desta, Z. The Cytochrome P450 2B6 (CYP2B6) Is the Main Catalyst of Efavirenz Primary and Secondary Metabolism: Implication for HIV/AIDS Therapy and Utility of Efavirenz as a Substrate Marker of CYP2B6 Catalytic Activity, J. Pharmacol. Exp. Ther., 2003, 306, 287-300, DOI: 10.1124/jpet.103.049601

What is claimed is:

1. A compound of

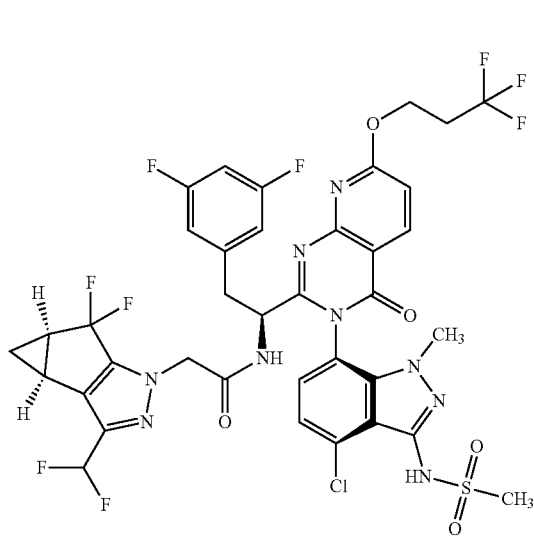

or a pharmaceutically acceptable salt thereof.

2. A pharmaceutical composition comprising the compound or pharmaceutically acceptable salt thereof according to claim 1 and a pharmaceutically acceptable excipient.

3. The pharmaceutical composition according to claim 2, wherein the composition is suitable for oral administration, for intramuscular injection, or for subcutaneous injection.

4. A method of treating HIV infection in a human comprising administration of an effective amount of the compound or pharmaceutically acceptable salt thereof according to claim 1 to the human.

5. The method of claim 4 wherein said administration is oral.

6. The method of claim 4 wherein said administration is intramuscular injection or subcutaneous injection.

7. The method of claim 4 wherein said method further comprises administration of at least one other agent used for treatment of HIV infection in a human.

8. The method of claim 7 wherein the at least one other agent is selected from the group consisting of abacavir, atazanavir, bictegravir, cabotegravir, dolutegravir, darunavir, doravirine, fostemsavir, lamivudine, maraviroc, rilpivirine, tenofovir disoproxil, tenofovir, and tenofovir alafenamide.

9. The method of claim 8 wherein the at least one other agent is selected from the group consisting of dolutegravir, lamivudine, fostemsavir, and cabotegravir.

10. A compound which is:

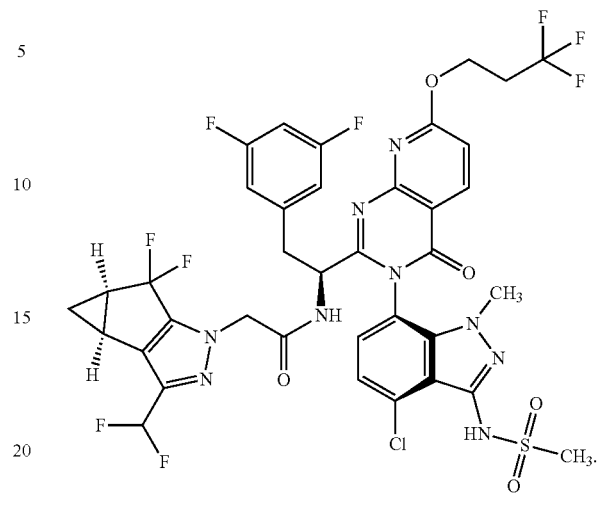

11. A pharmaceutical composition comprising the compound according to claim 10, and a pharmaceutically acceptable excipient.

12. The pharmaceutical composition according to claim 11, wherein the composition is suitable for oral administration, for intramuscular injection, or for subcutaneous injection.

13. A method of treating HIV infection in a human comprising administration of a therapeutically effective amount of the compound according to claim 10 to the human.

14. The method of claim 13 wherein said administration is oral.

15. The method of claim 13 wherein said administration is via intramuscular injection.

16. The method of claim 13 wherein said administration is via subcutaneous injection.

17. The method of claim 13 wherein said method further comprises administration of at least one other agent used for treatment of HIV infection in a human.

18. The method of claim 17 wherein the at least one other agent is selected from the group consisting of abacavir, atazanavir, bictegravir, cabotegravir, dolutegravir, darunavir, doravirine, fostemsavir, lamivudine, maraviroc, rilpiverine, tenofovir disoproxil, tenofovir, and tenofovir afenamide.

19. The method of claim 17 wherein the at least one other agent is selected from the group consisting of dolutegravir, lamivudine, fostemsavir, and cabotegravir.

20. The method of claim 17 wherein the at least one other agent is cabotegravir.

21. The method of claim 17 wherein the at least one other agent is dolutegravir.

* * * * *